US009067967B2

(12) United States Patent
García Antón et al.

(10) Patent No.: US 9,067,967 B2
(45) Date of Patent: Jun. 30, 2015

(54) PEPTIDES USEFUL IN THE TREATMENT AND CARE OF THE SKIN AND MUCOUS MEMBRANES AND THEIR USE IN COSMETIC OR PHARMACEUTICAL COMPOSITIONS

(75) Inventors: José María García Antón, Barcelona (ES); Nuria Almiñana Domenech, Barcelona (ES); Antonio Vicente Ferrer Montiel, Alicante (ES)

(73) Assignee: LIPOTEC, S.A., Gava-Barcelona (ES)

( * ) Notice: Subject to any disclaimer, the term of this patent is extended or adjusted under 35 U.S.C. 154(b) by 0 days.

(21) Appl. No.: 14/007,072

(22) PCT Filed: Mar. 23, 2012

(86) PCT No.: PCT/EP2012/055250
§ 371 (c)(1),
(2), (4) Date: Dec. 18, 2013

(87) PCT Pub. No.: WO2012/130771
PCT Pub. Date: Oct. 4, 2012

(65) Prior Publication Data
US 2014/0120141 A1 May 1, 2014

Related U.S. Application Data

(60) Provisional application No. 61/467,643, filed on Mar. 25, 2011.

(30) Foreign Application Priority Data

Mar. 25, 2011 (ES) .................................. 201130441

(51) Int. Cl.
| | |
|---|---|
| A61K 38/00 | (2006.01) |
| A61P 17/00 | (2006.01) |
| A61K 38/08 | (2006.01) |
| C07K 7/06 | (2006.01) |
| A61K 8/06 | (2006.01) |
| A61K 8/64 | (2006.01) |
| A61K 9/107 | (2006.01) |
| A61K 45/06 | (2006.01) |
| A61Q 19/00 | (2006.01) |
| A61Q 19/08 | (2006.01) |

(52) U.S. Cl.
CPC . *C07K 7/06* (2013.01); *A61K 38/00* (2013.01); *A61K 8/068* (2013.01); *A61K 8/64* (2013.01); *A61K 9/1075* (2013.01); *A61K 38/08* (2013.01); *A61K 45/06* (2013.01); *A61Q 19/007* (2013.01); *A61Q 19/08* (2013.01)

(58) Field of Classification Search
CPC ......... A61K 38/08; A61K 8/068; A61K 8/64; A61K 9/1075; C07K 7/06
See application file for complete search history.

(56) References Cited

U.S. PATENT DOCUMENTS

| | | | |
|---|---|---|---|
| 5,609,873 | A | 3/1997 | Meybeck et al. |
| 7,060,693 | B1 | 6/2006 | Dumas et al. |
| 8,039,028 | B2 | 10/2011 | Andre et al. |
| 8,450,456 | B2 | 5/2013 | Dal Farra et al. |
| 2007/0009474 | A1 | 1/2007 | Xie et al. |
| 2009/0130223 | A1 | 5/2009 | Breitenbach et al. |
| 2010/0261658 | A1 | 10/2010 | Dal Farra et al. |

FOREIGN PATENT DOCUMENTS

| | | | |
|---|---|---|---|
| EP | 1231893 | B1 | 8/2002 |
| EP | 1994923 | A2 | 2/2011 |
| FR | 2831058 | A1 | 4/2003 |
| FR | 28899949 | A1 | 3/2007 |
| FR | 2903015 | A1 | 1/2008 |
| FR | 2925500 | A1 | 6/2009 |
| FR | 2925501 | A1 | 6/2009 |
| FR | 2928090 | A1 | 9/2009 |
| JP | 2004-168732 | | 6/2004 |
| JP | 2005-343882 | A | 12/2005 |
| JP | 2006-290873 | A | 10/2006 |
| KR | 20080024868 | A | 3/2008 |
| WO | WO 2004/101609 | A2 | 11/2004 |
| WO | WO 2006/113681 | A2 | 10/2006 |
| WO | WO 2007/124991 | | 11/2007 |
| WO | WO 2009/106715 | A2 | 9/2009 |
| WO | WO 2009/106934 | A1 | 9/2009 |
| WO | WO 2010/091893 | * | 8/2010 |
| WO | WO 2010/091893 | A1 | 8/2010 |

OTHER PUBLICATIONS

Hara-Chikuma et al, Roles of Aquaporin-3 in the Epidermis, J Invest Dermatol. Sep. 2008;128(9):2145-51.*
Bellemere et al, Retinoic Acid Increases Aquaporin 3 Expression in Normal Human Skin, Journal of Investigative Dermatology (2008) 128, 542-548.*
Bellemere, et al. "Retinoic Acid Increases Aquaporin 3 Expression in Normal Human Skin", Journal of Investigative Dermatology, vol. 128, pp. 542-548 (2008).
Boury-Jamot, et al. "Expression and function of aquaporins in human skin: Is aquaporin-3 just a glycerol transporter?" Biochimica et Biophysica Acta 1758, pp. 1034-1042 (2006).
Brincat, et al. "A study of the decrease of skin collagen content, skin thickness, and Bone mass in the postmenopausal woman," Obstetrics & Gynecology, vol. 70, No. 6, pp. 840-845 Dec. 1987).

(Continued)

*Primary Examiner* — Karlheinz R Skowronek
*Assistant Examiner* — Sergio Coffa
(74) *Attorney, Agent, or Firm* — Fay Sharpe LLP

(57) ABSTRACT

Peptides of general formula (I), their stereoisomers, mixtures thereof and/or their cosmetically or pharmaceutically acceptable salts, a preparation process, cosmetic or pharmaceutical compositions which contain them and their use for the treatment and/or care of conditions, disorders and/or diseases of the skin and/or mucous membranes.

$$R_1-W_n-X_m-AA_1-AA_2-AA_3-AA_4-AA_5-AA_6-Y_p-Z_q-R_2 \quad (I)$$

21 Claims, No Drawings

(56) References Cited

OTHER PUBLICATIONS

Denda, et al. "Exposure to a dry Environment Enhances Epidermal permeability barrier function" The Society for Investigative Dermatology, Inc., 3(5) pp. 858-863 (1998).
Dumas, et al. "Histological variation of Japanese skin with aging," *International Journal of Cosmetic Science*, vol. 27, 37-79, pp. 47-50 (2005).
Fisher, et al. "Pathophysiology of Premature skin aging induced by ultraviolet light," *New England Journal of Medicine* 337(20) pp. 1419-1429 (1997).
Fisher, et al. "Ultraviolet irradiation increases matrix metalloproteinase-8 protein in human skin in vivo," *Journal of Investigative Dermatology* 117(2) pp. 219-226 (2001).
Flisiak, et al. "Effect of Psoriasis Activity on Metalloproteinase-1 and tissue inhibitor of metalloproteinase-1 in plasma and lesional scales," *Acta Dermato-Venereologica* 86(1) pp. 17-21 (2006).
Gorouhi, et al. "Role of topical peptides in preventing or treating aged skin," *In'tl. Journal of Cosmetic Science*, vol. 31(1) pp. 327-345 (Jan. 2009).
Hara, et al. "Selectively reduced glycerol in skin of aquaporin-3-deficient mice may account for impaired skin hydration, elasticity, and barrier recovery," Journal of Biological Chemistry, vol. 227, No. 48, pp. 46616-46621 (2002).
Hara, et al. "Glycerol replacement corrects defective skin hydration, elasticity, and barrier function in aquaporin-3-deficient mice" *Proceedings of the National Academy of Sciences* 100(12) pp. 7360-7365 (2003).
Jarrousse, et al., Identification of clustered cells in human hair follicle responsible for MMP-gelatinolytic activity: consequences for the regulation of hair growth, *Int'l. J. Dermatol.* vol. 40, pp. 385-392 (2001).
Katoh, et al. "Increased levels of serum tissue inhibitor of metalloproteinase-1 but not metalloproteinase-3 in atopic dermatitis," *Clinical & Experimental Immunology*, 127(2) pp. 283-288 (2002).
Ma, et al. "Impaired stratum corneum hydration in mice lacking epidermal water channel Aquaporin-3," *Journal of Biological Chemistry*, vol. 227, No. 19, pp. 17147-17153 (May 2002).
Rawlings, et al. "Abnormalities in stratum corneum structure, lipid composition, and desmosome degradation in soap-induced winter xerosis", J. Soc. Cosmet. Chem., vol. 45, pp. 203-220 (1994).
Rojek, et al. "A current view of the Mammalian Aquaglyceroporins", *Annu. Rev. Physiol.* 70, pp. 301-327 (2008).
Kerkelä, et al. "Matrix metalloproteinase in tumor progression: focus on basal and squamous cell skin cancer," *Experimental Dermatology*, vol. 12, pp. 109-125 (2003).
Sato, et al. "Dry condition affects desquamation of stratum corneum in vivo" *Journal of Dermatological Science* 18, pp. 163-169 (1998).
Sato, et al. "Roles of membrane-type matrix metalloproteinase-1 in tumor invasion and metastatis" *Cancer Science* 96(4) pp. 212-217 (2005).
Sougrat, et al. "Functional Expression of AQP3 in Human Skin Epidermis and Reconstructed Epidermis," *Journal of Investigative Dermatology* 118(4) pp. 678-685 (2002).
Tagami, et al. "Quantitative measurements of water concentration of the stratum corneum in vivo by high-frequency current," *Acta Dermato-Venereologica, Suppl.* 185, pp. 29-33 (1994).
Takenouchi, et al. "Hydration Characteristics of Pathologic Stratum Corneum-Evaluation of Bound Water," *Journal of investigative dermatology* 87(5) 574-576 (1986).
Zheng, et al. "Aquaporin 3 colocates with phospholipase $D_2$ in Caveolin-Rich Membrane Microdomains and is downregulated upon keratinocyte differentiation," *J. Investigative Dermatology*, pp. 1487-1495 (2003).
Denda, et al., "Low humidity stimulates epidermal DNA synthesis and amplifies the hyperproliferative response to barrier disruption: implication for seasonal exacerbations of inflammatory dermatoses," J. Invest. Dermatol. 111 pp. 873-878 (1998).
Watanabe et al., "Functional analyses of the superficial stratum corneum in atopic xerosis," Arch. Dermatol. 127 pp. 1689-1692 (1991).
Thune, "Evaluation of the hydration and the water-holding capacity in atopic skin and so-called dry skin," Acta Derm. Venereol. Suppl. (Stockh) 144 pp. 133-135 (1989).
Horrii, et al., "Stratum corneum hydration and amino acid content in xerotic skin," Br. J. Dermatol. 121 pp. 587-592, (1989).
Hara, et al., "Amelanotic acral melanoma masquerading as fibrous histiocytic tumours. Three case reports," Acta Derm. Venereol., 73, pp. 283-285 (1993).
IUPAC IUB Commission of Biochemical Nomenclature specified in Eur. J. Biochem. 138:9 p. 9-37 (1984).
Roberts, et al., "The Peptides", vol. 5, Chapter VI, Gross E. and Meienhofer J., Eds., Academic Press, New York, USA, pp. 341-449 (1983).
Berge et al., "Pharmaceutical Salts," J. Pharm. Sci. 66 pp. 1-19 (1977).
Stewart, et al., "Solid Phase Peptide Synthesis, 2nd edition", Pierce Chemical Company, Rockford, Illinois, pp. 1-9 and 71-95 (1984).
Bodansky, et al., "The practice of Peptide Synthesis," Springer Verlag, New York pp. 77-126 (1984).
Lloyd-Williams, et al., "Chemical Approaches to the Synthesis of Peptides and Proteins," CRC, Boca Raton, FL, USA, pp. 19-93 (1997).
Kullmann, "Proteases as catalysts for enzymic syntheses of opioid peptides," J.Biol.Chem. 255 pp. 8234-8238 (1980).
Lloyd-Williams, et al., "Convergent solid phase peptide synthesis," Tetrahedron 49 pp. 11065-11133 (1993).
Atherton, et al., "Solid Phase Peptide Synthesis: A practical approach," IRL Oxford University Press, pp. 1-61 (1989).
Matsueda et al, "A p-methylbenzhydrylamine resin for improved solid-phase synthesis of peptide amides," Peptides 2, pp. 45-50 (1981).
Barlos et al., "Darstellung geschützter Peptid-Fragmente unter Einsatz substituierter Triphenylmethyl-Harze," Tetrahedron Lett., 30, pp. 3943-3946 (English Summary only), (1989).
Barlos et al., "Veresterung von partiell geschützten Peptid-Fragmenten mit Harzen. Einsatz von 2-Chlorotritylchlorid zur Synthese von Leu1-Gastrin I," Tetrahedron Lett., 30, pp. 3947-3951 (English Summary only) (1989).
Albericio, et al., "Preparation and application of the 5-(4-(9-fluorenylmethyloxycarbonyl) aminomethyl-3,5-dimethoxy-phenoxy)valeric acid (PAL) handle for the solid-phase synthesis of C-terminal peptide amides under mild conditions," J. Org. Chem., 55 pp. 3730-3743 (1990).
Rink, "Solid-phase synthesis of protected peptide fragments using a trialkoxy-diphenyl-methylester resin," Tetrahedron Lett., 28 pp. 3787-3790 (1987).
Wang, "p-Alkoxybenzyl Alcohol Resin and p-Alkoxybenzyloxycarbonylhydrazide Resin for Solid Phase Syntheis of Protected Peptide Fragments," J.Am.Chem., 95, pp. 1328-1333 (1973).
Wilkinson, et al., "Harry's Cosmeticology," Seventh edition, Longman House, Essex, GB pp. 50-73 and 757-799 (1982).
Schaab, "Impregnating Fabrics With Microcapsules," HAPPI May, pp. 84-86 (1986).
Nelson, "Application of microencapsulation in textiles," Int. J. Pharm., 242 pp. 55-62 (2002).
Hipler, "Biofunctional Textiles and the Skin," Curr. Probl. Dermatol., v.33, pp. 34-41 and 144-151 (2006).
Malcom, et al., "Controlled release of a model antibacterial drug from a novel self-lubricating silicone biomaterial," J. Cont. Release, 97 pp. 313-320 (2004).
Gottschalck, "CTFA International Cosmetic Ingredient Dictionary & Handbook," 12th Edition, pp. 3040-3065 (2008).
Kaiser, et al., "Color Test for Detection of Free Terminal Amino Groups in the Solid-Phase Synthesis of Peptides," pp. 595-598 (1970).

(56) References Cited

OTHER PUBLICATIONS

Christensen, "A Qualitative Test for Monitoring Coupling Completeness in Solid Phase Peptide Synthesis Using Chloranil," Acta Chem. Scand. 33B: pp. 763-766 (1979).

Juan, et al., "Aquaporin-3 expression decreases with ageing and sun-exposure in the human epidermis," Journal of Investigative Dermatology, vol. 125, No. 3, p. A57 (2005). Abstract only.

Miyoshi, et al., "Beneficial Effects of Tissue Inhibitor of Mealloproteinases-2 (TIMP-2) on Chronic Dermatitis," J. Dermatology, vol. 32, pp. 346-353 (2005).

Fluhr, et al., "Glycerol Regulates Stratum Conrneum Hydration in Sebaceous Gland Deficient (Asebia) Mice," Society for Investigative Dermatology, pp. 728-737 (2003).

Rogers, et al., "Stratum corneum lipids: the effect of ageing and the seasons," Arch. Dermatol. Res., vol. 288, pp. 765-770 (1996).

* cited by examiner

SEQUENCE LISTING

```
<160> NUMBER OF SEQ ID NOS: 62

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Ala Ser Pro Ala Gly Gly Pro
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Gly Ser Pro Ala Gly Gly Pro Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Ile Ser Val Ala Gly Gly Gly Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Ile Ser Val Ala Gly Gly His
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ser Pro Ala Glu Gly Gln
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Ser Pro Ala Glu Gly Gly
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ser Pro Ala Gly Gly Gln Ala
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Ser Pro Ala Gly Gly Gln
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ser Pro Ala Gly Gly Pro Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Ser Pro Ala Gly Gly Pro
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Ser Pro Ala Val Ala Gly Gly Ala
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Ser Val Ala Glu Gly Gln
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Ser Val Ala Gly Gly Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Ser Val Ala Val Ala Gln
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Ser Val Ala Val Gly Gln
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Ser Val Ala Val Gly Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Ser Val Ala Val Gly Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Ser Val Gly Glu Gly His
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Ser Val Gly Val Gly Gln
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Thr Pro Ala Gly Gly Pro
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Thr Pro Gly Gly Gly Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Tyr Pro Ala Glu Gly Gln
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Tyr Pro Ala Glu Gly Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Tyr Pro Ala Glu Gly Pro
1               5
```

```
<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Tyr Pro Ala Gly Gly Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Tyr Pro Ala Gly Gly Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

Tyr Pro Ala Gly Gly Val
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Tyr Pro Ala Val Gly Gln
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Tyr Pro Ala Val Gly Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Tyr Pro Ala Val Gly His
1               5
```

```
<210> SEQ ID NO 31
<211> LENGTH: 6
<212> TYPE: PRT
<213> ORGANISM: Artificial Sequence
<220> FEATURE:
<223> OTHER INFORMATION: Synthetic peptide

<400> SEQUENCE: 31

Tyr Pro Ala Val Gly Pro
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide

<400> SEQUENCE: 32

Tyr Val Ala Glu Gly Pro
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide

<400> SEQUENCE: 33

Tyr Val Ala Gly Gly Gly
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide

<400> SEQUENCE: 34

Tyr Val Ala Gly Gly His
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide

<400> SEQUENCE: 35

Tyr Val Ala Gly Gly Pro
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Tyr Val Ala Val Gly Gly
1               5
```

```
<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

Val Ser Pro Ala Val Gly Gln
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Ser Val Ala Gly Gly Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide

<400> SEQUENCE: 39

Ser Pro Ala Val Gly Gln
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Ser Pro Ala Val Gly Gly
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide

<400> SEQUENCE: 41

Ser Val Ala Gly Gly His
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide

<400> SEQUENCE: 42

Tyr Val Ala Gly Gly Gln
1               5
```

```
<210> SEQ ID NO 43
<211> LENGTH: 6
<212> TYPE: PRT
<213> ORGANISM: Artificial Sequence
<220> FEATURE:
<223> OTHER INFORMATION: Synthetic peptide

<400> SEQUENCE: 43

Tyr Pro Ala Gly Gly Gln
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide

<400> SEQUENCE: 44

Tyr Val Ala Glu Gly His
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide

<400> SEQUENCE: 45

Ser Pro Ala Gly Gly His
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide

<400> SEQUENCE: 46

Ser Val Ala Glu Gly Gly
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide

<400> SEQUENCE: 47

Tyr Pro Ala Gly Gly His
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide

<400> SEQUENCE: 48

Ser Pro Ala Glu Gly His
1               5
```

```
<210> SEQ ID NO 49
<211> LENGTH: 6
<212> TYPE: PRT
<213> ORGANISM: Artificial Sequence
<220> FEATURE:
<223> OTHER INFORMATION: Synthetic peptide

<400> SEQUENCE: 49

Ser Pro Ala Val Gly Pro
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide

<400> SEQUENCE: 50

Ser Val Ala Gly Gly Gln
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

Tyr Val Ala Val Gly Gln
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide

<400> SEQUENCE: 52

Tyr Val Ala Val Gly His
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide

<400> SEQUENCE: 53

Ser Pro Ala Glu Gly Pro
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide

<400> SEQUENCE: 54

Tyr Val Ala Val Gly Pro
1               5
```

```
<210> SEQ ID NO 55
<211> LENGTH: 6
<212> TYPE: PRT
<213> ORGANISM: Artificial Sequence
<220> FEATURE:
<223> OTHER INFORMATION: Synthetic peptide

<400> SEQUENCE: 55

Ser Val Ala Val Gly His
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide

<400> SEQUENCE: 56

Tyr Val Ala Glu Gly Gly
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide

<400> SEQUENCE: 57

Tyr Pro Ala Glu Gly His
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide

<400> SEQUENCE: 58

Ser Val Ala Glu Gly His
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide

<400> SEQUENCE: 59

Ser Pro Ala Val Gly His
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic peptide

<400> SEQUENCE: 60

Ser Val Ala Glu Gly Pro
1               5
```

```
<210> SEQ ID NO 61
<211> LENGTH: 6
<212> TYPE: PRT
<213> ORGANISM: Artificial Sequence
<220> FEATURE:
<223> OTHER INFORMATION: Synthetic peptide

<400> SEQUENCE: 61

Tyr Val Ala Glu Gly Gln
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide

<400> SEQUENCE: 62

Ser Pro Ala Gly Gly Gly
1               5
```

PEPTIDES USEFUL IN THE TREATMENT AND CARE OF THE SKIN AND MUCOUS MEMBRANES AND THEIR USE IN COSMETIC OR PHARMACEUTICAL COMPOSITIONS

This application claims the priority and benefit of International Application PCT/EP2012/055250, filed Mar. 23, 2012, ES 201130441, filed Mar. 25, 2011, and U.S. Application Ser. No. 61/467,643, filed Mar. 25, 2011, from which the PCT application claims priority, the disclosures of which are incorporated herein by reference in their entireties.

FIELD OF THE INVENTION

This invention relates to peptides capable of modulating aquaporin-3 (AQP-3) and/or stimulating collagen synthesis in the skin and/or mucous membranes and cosmetic or pharmaceutical compositions which contain these peptides which are useful in the treatment and/or care of the skin and/or mucous membranes, preferably for the treatment and/or care of conditions, disorders and/or pathologies of the skin and/or mucous membranes which improve or are prevented by AQP-3 modulation and/or stimulation of collagen synthesis.

BACKGROUND OF THE INVENTION

The epidermis is the outermost layer of the skin. Its cells are differentiated to provide a waterproof mechanical barrier, crucial to enable life on Earth. Due to its contact with the outside, the epidermis suffers damage more frequently and directly than any other tissue in the body, therefore its organization depends on the mechanisms ability to repair and renew.

The epidermis has a stratified organization with three layers or principal strata (stratum basale, stratum granulosum and stratum corneum), and is due to the strong balance between the proliferation and differentiation of keratinocytes. When the cells in the basal layer undergo differentiation they lose their proliferative capacity and move progressively closer to the stratum corneum. The stratum basale is composed of keratinocytes, and their characteristic activity is the synthesis of keratin, a protein which forms intermediary filaments and is responsible for giving the epidermis its hardness. Several layers of spur cells are found on this stratum basale layer and a stratum granulosum cell layer is located on the spur cell layers. The granulosum cell layer is crucial for maintaining the impermeability of the epidermis, which is its most important function. The granulosum cell layer, furthermore, marks the limit between metabolically active cells and dead cells. Such dead cells result from the progressive loss of organelles and the filling of its cytoplasms with keratin as they advance towards the outside, the cells being reduced to flat scales completely filled with densely packed keratin. These dead cells become detached from the surface of the skin approximately one week after emerging from the basal layer. This particular organization of the stratum corneum serves to protect the skin, and in turn allows it to maintain a certain level of flexibility retaining a defined quantity of water. Hydration of the stratum corneum is crucial to determine the appearance, metabolism, mechanical properties and the skin's function as a barrier.

Aging of the skin is a complex process which comprises two differentiated processes, intrinsic and extrinsic aging. The former is due to genetic factors and does not just affect the skin but all the body's organs. Extrinsic aging is caused by environmental factors, such as exposure to contamination, tobacco smoke, ultraviolet radiation, wind, cold climates, etc. Both processes overlap on areas of the skin exposed to the outside, and share chemical processes. Aging and skin aging is understood to be the appearance of visible changes to the appearance of the skin, as well as those which are discernible by touch, such as and not restricted to, the development of discontinuities on the skin such as wrinkles, fine lines, expression lines, stretch marks, striae, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin.

One of the clearest signs of aging is the appearance of wrinkles, due both to the loss of collagen and the loss of the skin's elasticity. At an ultrastructural level, the skin's collagen network becomes denser with age, despite the loss of total collagen content. The elastic fibers progressively decline and break into fragments, which leads to the loss of the skin's elasticity and the appearance of wrinkles. The process begins in phases relatively early on in life, and accelerates after forty. It has been proven that women lose 2.1% of their collagen level per year after the menopause and that 30% of the collagen is lost in the first five years after the menopause [Brincat M. et al., "*A study of the decrease of skin collagen content, skin thickness, and bone mass in the postmenopausal woman*" Obstet. Gynecol., (1987), 70, 840-845]. Therefore, an increase in the quantity of wrinkles and fine lines is observed, a loss of flexibility of the skin and women experience a feeling of "dry skin" or tight skin.

This process is aggravated by the action of the family of matrix metalloproteinases (MMP), a family of proteolytic enzymes (endoproteinases) which can collectively degrade the macromolecular components of the extracellular matrix (collagen and elastin) and the basal lamina. The degradation of the collagen fibers leads to skin with a sagging and wrinkly appearance, especially in the areas exposed to sunlight, such as the skin on the face, ears, neckline, scalp, hands and arms, which is not desirable.

Furthermore, prolonged exposure to ultraviolet radiation, particularly UVA and UVB, stimulates MMP synthesis, which destroy collagen [Fisher G. J. et al., "*Pathophysiology of premature skin aging induced by ultraviolet light*". New Eng. J. Med., (1997), 337, 1419-1429; Fisher G. J., "*Ultraviolet irradiation increases matrix metalloproteinase-8 protein in human skin in vivo*". J. Invest. Dermatol., (2001), 117, 219-226], which is one of the principal causes of photoaging.

One of the causes of different conditions, disorders and diseases of the skin and/or mucous membranes are found in low levels of collagen, either due to its diminished synthesis, or due to the increase in its degradation. Among them we can highlight chronic ulcers, psoriasis [Flisiak I. et al., "*Effect of psoriasis activity on metalloproteinase-1 and tissue inhibitor of metalloproteinase-1 in plasma and lesional scales*". Acta Derm Venereol., (2006), 86, 17-21], oral conditions such as gingivitis and periodontitis, skin cancer [Kerkelä E. et al., "*Matrix metalloproteinases in tumor progression: focus on basal and squamous cell skin cancer*". Exp Dermatol., (2003), 12, 109-125], metastasis [Sato H. et al., "*Roles of membrane-type matrix metalloproteinase-1 in tumor invasion and metastasis*". *Cancer Sci.*, (2005), 96, 212-217], dermatitis [Katoh N. et al., "*Increased levels of serum tissue inhibitor of metalloproteinase-1 but not metalloproteinase-3 in atopic dermatitis*". *Clin. Exp. Immunol.*, (2002), 127, 283-288], rosacea, telangiectasia, couperosis, bags under the eyes, periorbital dark circles, varicose veins, alopecia [Jarrousse F. et al., "*Identification of clustered cells in human hair follicle responsible for MMP-9 gelatinolytic activity: consequences for the regulation of hair growth*". *Int. J. Dermatol.*, (2001), 40, 385-392] cellulitis, orange peel skin, healing or re-epithelialization disorders, and stretch marks, among others. Dermatitis includes skin conditions, disorders or diseases which cause inflammation, such as contact dermatitis, atopic dermatitis, sensitive skin and eczema. Therefore, all these conditions, disorders and diseases are treatable with compounds stimulating collagen synthesis.

The loss of hydration in aged and photoaged skin is another of the causes of the appearance of wrinkles on the skin, as well as the change to the skin barrier function. The skin's water content can influence lipid synthesis [Rawlings A. V. et al., "*Abnormalities in stratum corneum structure lipid composition and desmosome degradation in soap-induced winter xerosis*". *J. Soc. Cosmet. Chem.*, (1994), 45, 203-220], in epidermal DNA synthesis [Denda M. et al., "*Low humidity stimulates epidermal DNA synthesis and amplifies the hyperproliferative response to barrier disruption: implication for seasonal exacerbations of inflammatory dermatoses*". *J. Invest. Dermatol.*, (1998), 111, 873-878], in its function as a barrier [Denda M. et al., "*Exposure to a dry environment enhances epidermal permeability barrier function*". *J. Invest. Dermatol.*, (1998), 111, 858-863] and in the thickness of the skin [Sato J. et al., "*Dry condition affects desquamation of stratum corneum in vivo*". *J. Dermatol. Sci.*, (1998), 18, 163-169]. Natural moisturizing factors (NMF) are found in the stratum corneum, which are a mixture of molecules with hygroscopic properties that favor water retention. Generally speaking, the skin's water content varies according to where the sample is taken; therefore, the content in the basal and suprabasal layers of living cells is approximately 75%, whilst the content in the stratum corneum is reduced by up to 10-15%. The relative humidity in the atmosphere, the epidermis' capacity to compensate the loss of water by evaporation and the intrinsic capacity of the stratum corneum to retain water are other factors which determine the skin's water content. Although the mechanisms which govern the transportation of water through the epidermis are still not completely clear, the existence of a continual exchange of water between the stratum corneum, the living cells in the underlying skin and the atmosphere seems to be clear, a process in which it is known that there are several factors involved. Of them, the composition of the stratum corneum, including its content of low molecular weight osmolytes or other molecules such as free amino acids, is particularly relevant, as the existence of a high concentration of $Na^+$, $K^+$ and $Cl^-$ ions and a low concentration of water in the superficial part of the stratum corneum has been proven, which would generate gradients of water and solutes from the surface of the skin to the epidermal keratinocytes. The protein AQP-3 is considered the principal protein responsible for facilitating transepidermal permeability to protect the stratum corneum from drying due to the loss of water or from the dissipation of water gradients in the layer of epidermal keratinocytes.

AQP-3 is a member of the family of homologous integral membrane proteins and of the sub-class of aquaglyceroporins responsible for facilitating the transportation of water, glycerol, and other small solutes (e.g. urea), through biological membranes. In mammals, the family of aquaporins comprises 13 homologous proteins (AQP-1 to AQP-13) which can be classified into 3 groups: water channels, aquaglyceroporins and unorthodox aquaporins. Water channels can only transport water, aquaglyceroporins can transport water and glycerol, and, on occasions other small solutes; the aquaporins in the third group have specific properties, or they have not been clarified [Rojek A. et al., "*A current view of the mammalian aquaglyceroporins*" *Annu. Rev. Physiol.*, (2008), 70, 301-327]. A wide spectrum of aquaporins can be found in mammals' skin, AQP-3 being the most abundant in human epidermis [Sougrat R. et al., "*Functional expression of AQP-3 in human skin epidermis and reconstructed epidermis*", *J. Invest. Dermatol.*, (2002), 118, 678-685]. AQP-3 is present not only in skin but also in tissue in the urinary tract, in the respiratory tract, in the digestive tract and in others, such as in collecting ducts.

There are different hypotheses of the molecular mechanisms through which AQP-3 acts. It is believed that the transportation of water in the skin occurs along an osmotic gradient under the stratum corneum, where permeability is mediated by AQP-3. The variations in the pH in the different layers of the skin, with values which can vary from 5 to 7 under the stratum corneum, allow the permeability of the skin to be modulated, as is the case of the marked impermeability in the granulo-corneoepidermal interface. In this context, the transported water would have an immobilizing effect on the layers of viable epidermal cells, which would promote hydration of the cutaneous layers which lay beneath the stratum corneum. There is a low concentration of water and a high concentration of solutes in the latter, responsible for generating a gradient of water and solutes between the outermost layer of the skin and the layer of viable keratinocytes [Takenouchi M. et al., "*Hydration characteristics of pathologic stratum corneum-evaluation of bound water*", *J. Invest. Dermatol.*, (1986), 87, 574-576]. It is believed that AQP-3 participates in the improvement of transepidermal permeability to protect the stratum corneum from the evaporation of water from the surface of the skin. Another possibility is that AQP-3 has a role in the dispersion of water gradients through the width of the layer of epidermal keratinocytes. The discontinuity of the water content between the stratum granulosum and the stratum corneum enables the existence of highly organized lipid-water lamellar structures located between corneocytes, that are crucial structures for the maintenance of the skin's barrier of permeability.

One of the phenotypic features characteristic in knockout mice deficient in AQP-3 is the dryness of the skin, which is one of the best proofs of the roles of AQP-3 in the hydration of the stratum corneum and, therefore, of the epidermis. Other changes to the skin which accompany the deficiency of AQP-3 are a reduction in elasticity, a delay in the recovery of the barrier functions, and a delay in the healing time of wounds [Hara M. et al., "*Glycerol replacement corrects defective skin hydration, elasticity, and barrier function in aquaporin-3-deficient mice*". *Proc. Natl. Acad. Sci. USA.*, (2003), 100, 7360-7365; Ma T. et al., "*Impaired stratum corneum hydration in mice lacking epidermal water channel aquaporin-3*". *J. Biol. Chem.*, (2002), 277, 17147-17153; Hara M. et al., "*Selectively reduced glycerol in skin of aquaporin-3-deficient mice may account for impaired skin hydration, elasticity, and barrier recovery*". *J. Biol. Chem.*, (2002), 277, 46616-46621]. AQP-3 also has an important role in the regulation of the differentiation and proliferation of keratinocytes [Bellemère G. et al., "*Retinoic acid increases aquaporin 3 expression in normal human skin*". *J. Invest. Derma-* tol., (2008), 128, 542-548], contributing to the maintenance of the skin barrier function. AQP-3 co-localizes with phospholipase D2 in caveolin-rich membrane microdomains, and provides phospholipase 2 with glycerol to generate phosphatidylglycerol, which, in turn, can initiate early differentiation [Zheng X. et al., "*Aquaporin* 3 *colocates with phospholipase d2 in caveolin-rich membrane microdomains and is downregulated upon keratinocyte differentiation*". *J. Invest. Dermatol.*, (2003), 121, 1487-1495].

One of the causes of the different conditions, disorders and diseases of the skin and/or mucous membranes is a reduction of the skin's water content. Among them we can highlight atopic dermatitis [Watanabe M. et al., "*Functional analyses of the superficial stratum corneum in atopic xerosis*". *Arch. Dermatol.*, (1991), 127, 1689-1692], eczema [Thune P., "*Evaluation of the hydration and the water-holding capacity in atopic skin and so-called dry skin*". *Acta Derm. Venereol. Suppl. (Stockh).*, (1989), 144, 133-135], psoriasis [Tagami H., "*Quantitative measurements of water concentration of the stratum corneum in vivo by high-frequency current*". *Acta Derm. Venereol. Suppl. (Stockh)*, (1994), 185, 29-33], plantar hyperkeratosis, senile xerosis, [Horii I. et al., "*Stratum corneum hydration and amino acid content in xerotic skin*". *Br. J. Dermatol.*, (1989), 121, 587-592], hereditary ichthyosis [Hara M. et al., "*Amelanotic acral melanoma masquerading as fibrous histiocytic tumours. Three case reports*". *Acta Derm. Venereol.*, (1993), 73, 283-285], changes to the epidermis such as spongiosis [Boury-Jamot M. et al., "*Expression and function of aquaporins in human skin: Is aquaporin-3 just a glycerol transporter?*". *Biochim. Biophys. Acta*, (2006), 1758, 1034-1042] or vaginal dryness [KR20080024868 A] among others. All these conditions, disorders and diseases are, therefore, treatable with compounds which modulate AQP-3.

A relationship between AQP-3 and the skin's aging and photoaging has also been established. It has been proven that the epidermis experiences a reduction in AQP-3 expression in accordance with age and exposure to solar radiation [Dumas M. et al., "*Histological variation of Japanese skin with ageing*". *Int. J. Cosm. Sci.*, (2005), 27, 47-50].

Therefore, collagen fibers and hydration in the skin and/or mucous membranes are of great importance in maintaining the skin's balance and being able to reduce, delay and/or prevent the signs of aging and/or photoaging. It is important to have products available, whose effects are intended to maintain the levels of collagen and/or the hydration of the skin, and the maintenance of a smooth and firm appearance of the skin reducing, delaying and/or preventing the signs of aging and/or photoaging. The maintenance of a high collagen content in the skin or hydration of the skin can be achieved in many different ways. On the one hand, substances which induce collagen synthesis to counteract the negative effects of the skin's degradation with age can be used. Substances which modulate AQP-3 to increase the skin's hydration can also be used.

In the prior art there are active ingredients effective as instigators of collagen synthesis, such as ascorbic acid and its derivatives, in particular, ascorbyl palmitate, magnesium ascorbyl phosphate, sodium ascorbyl phosphate, and ascorbyl alpha- and beta-glucoside, retinol and derivatives of retinol such as retinoic acid, retinal, retinol, retinyl acetate, retinyl palmitate or plant extracts such as extracts of *Aloe* spp or *Centella* spp. The group of active ingredients frequently used to induce collagen synthesis also includes peptides and peptide derivatives such as carnitine, carnisine, peptides including peptides derived from matrikine (e.g. lysyl-threonyl-threonyl-lysyl-serine). In addition, compounds such as asiatic acid, madecassic acid, madecassoside, asiaticoside, extracts of *Centella asiatica*, niacinamide, astaxanthin, glucans e.g. from yeast and oat (*Avena sativa*), extract of soy (*Glycine max*), soy isoflavones e.g. genistein, daidzein, rutin, chrysin, morin, alkaloids of the areca nut, forskolin, betulinic acid, extracts of *Plantago* spp, TGF-beta, extracts of *Ginkgo biloba*, glutamine, and glycolic acid are used as stimulators of collagen synthesis.

There are also a number of compounds on the market capable of increasing the levels of aquaporins in the skin to palliate the symptoms of disorders related to its deficiency. The cosmetic and pharmaceutical industry is aware of this and has made considerable efforts to find molecules or extracts which bring about an increase in AQP-3 expression in the skin, such as xanthine, caffeine, ginsenosides, vitamin B3 or niacin [US 2007/0009474 A1], vitamin A or retinoic acid/all-trans retinoic acid (ATRA) [Bellemère G. et al., "*Retinoic acid increases aquaporin* 3 *expression in normal human skin*". *J. Invest. Dermatol.*, (2008), 128, 542-548], tocopheryl retinoate [JP 2006-290873 A], steroid derivatives, specifically the use of ecdysteroids [U.S. Pat. No. 5,609,873 A; U.S. Pat. No. 7,060,693 B1], glyceryl glucosides [WO 2007/124991 A1], glyceryl glycosides [US 2009/0130223 A1], peptides derived from the sequence of aquaporins [FR 2925500 A1], certain synthetic peptides [FR 2925501 A1], extract of *Ajuga turkestanica* [EP 1231893 B1], extract of *Pyrus malus* [FR 28899949 A1], extract of *Vanda coerulea* [FR 2928090 A1], extracts of brown algae such as *Undaria pinnatifida* [FR 2903015 A1], extract of *Laminaria digitata* [EP 1994923 A2], extract of *Piptadenia colubrina* [WO 2009/106934 A1], extracts of plants from the Tropaeolaceae family and of the species *Crocus sativus* [JP 2004-168732 A; JP 2005-343882 A] or extract of *Punica granatum* [FR 2831058 A1], among others.

However, despite the arsenal of existing compounds and/or extracts, the cosmetic, pharmaceutical and food sector is still interested in developing alternatives to the compounds known in the prior art, capable of stimulating collagen synthesis and/or increasing the hydration of the skin and/or mucous membranes.

BRIEF DESCRIPTION

In accordance with one aspect of the exemplary embodiment, a peptide of general formula (I)

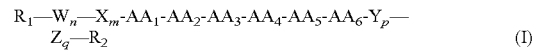

$$R_1-W_n-X_m-AA_1-AA_2-AA_3-AA_4-AA_5-AA_6-Y_p-Z_q-R_2 \quad (I)$$

its stereoisomers, mixtures thereof and/or its cosmetic or pharmaceutical acceptable salts is disclosed, wherein:

$AA_1$ is selected from the group consisting of -Ser-, -Thr- and -Tyr-;

$AA_2$ is selected from the group consisting of -Pro- and -Val-;

$AA_3$ is -Ala-;

$AA_4$ is selected from the group consisting of -Glu-, -Gly- and -Val-;

$AA_5$ is -Gly-;

$AA_6$ is selected from the group consisting of -Gln-, -Gly-, -His- and -Pro-;

W, X, Y, Z are amino acids and are independently selected from amongst themselves;

n, m, p and q are independently selected from amongst themselves and have a value of 0 or 1;

n+m+p+q is lower than or equal to 2;

$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl, and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that $R_1$ and $R_2$ are not α-amino acids.

DETAILED DESCRIPTION OF THE INVENTION

This invention provides a solution to the above-mentioned problem. Surprisingly, the applicant of this invention has found that aquaporin expression and/or stimulation of collagen synthesis can be modulated by certain synthetic peptides. Therefore, the inventors have determined that these synthetic peptides are capable of modulating aquaporin AQP-3 and/or stimulating collagen synthesis. The peptides are useful for the treatment and/or care of those conditions, disorders and/or diseases which improve or are prevented by AQP-3 modulation and/or by collagen synthesis stimulation, improving the skin hydration, the skin barrier function and/or treating, preventing and/or repairing the signs of aging and/or photoaging of the skin.

Definitions

In order to facilitate the comprehension of this invention, the meanings of some terms and expressions as used in the context of the invention are included.

In the context of this invention "AQP-3 modulation" is understood to be both the increase and decrease of AQP-3 synthesis and the increase or inhibition of its activity.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term skin includes the scalp.

The term "treatment", as used in the context of this report, refers to the administration of a peptide according to the invention to alleviate or eliminate a disease or disorder or reduce or eliminate one or more symptoms associated with this disease or disorder. The term "treatment" also covers the ability to alleviate or eliminate the physiological consequences of the disease or disorder.

In the context of this invention "care" comprises the prevention of diseases and/or disorders.

The term "prevention", as used in this invention, refers to the ability of a peptide of the invention to prevent, delay, or hinder the appearance or development of a disease or disorder before its appearance.

In the context of this invention, the term "aging" refers to the changes experienced by the skin with age (chronoaging) or through exposure to the sun (photoaging) or to environmental agents such as tobacco smoke, extreme climatic conditions of cold or wind, chemical contaminants or pollutants, and includes all the external visible and/or perceptible changes through touch, such as and not restricted to, the development of discontinuities on the skin such as wrinkles, fine lines, expression lines, stretch marks, striae, furrows, irregularities or roughness, increase in the size of pores, loss of moisture, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of different environmental factors such as exposure to tobacco smoke, exposure to pollution, and climatic conditions such as cold and/or wind also contributes to the aging of the skin.

In this description the abbreviations used for amino acids follow the rules of the IUPAC-IUB Commission of Biochemical Nomenclature specified in *Eur. J. Biochem.* (1984) 138:9-37.

Thus, for example, Ala represents $NH_2$—$CH(CH_3)$—COOH, Ala- represents $NH_2$—$CH(CH_3)$—CO—, -Ala represents —NH—$CH(CH_3)$—COOH and -Ala- represents —NH—$CH(CH_3)$—CO—. Therefore, the hyphen, which represents the peptide bond, eliminates the OH in the 1-carboxyl group of the amino acid (represented here in the conventional non-ionized form) when situated to the right of the symbol, and eliminates the H in the 2-amino group of the amino acid when situated to the left of the symbol; both modifications can be applied to the same symbol (see Table 1).

TABLE 1

Structures of amino acid residues and their nomenclature in one and three-letter code

| Name | Residu-e | Symbol | Residue |
|---|---|---|---|
| Alanyl- Ala- A | HN—CH(CH₃)—C(=O) | Gluta- minyl- Gln- Q | HN—CH(CH₂CH₂C(=O)NH₂)—C(=O) |
| Gluta-myl- Glu- E | HN—CH(CH₂CH₂COOH)—C(=O) | Glycyl- Gly- G | HN—CH(H)—C(=O) |

TABLE 1-continued

Structures of amino acid residues and their nomenclature in one and three-letter code

| Name | Residu-e | Symbol | Residue |
|------|----------|--------|---------|
| Histidyl- His- H | | Prolyl- Pro- P | |
| Seryl- Ser- S | | Threonyl- Thr- T | |
| Tyrosyl- Tyr- Y | | Valyl- Val- V | |

The abbreviation "Ac-" is used in this description to denote the acetyl group ($CH_3$—CO—) and the abbreviation "Palm-" is used to denote the palmitoyl group ($CH_3$—$(CH_2)_{14}$—CO—).

The term "non-cyclic aliphatic group" is used in this invention to cover, for example and not restricted to, the linear or branched alkyl, alkenyl and alkynyl groups.

The term "alkyl group" refers to a saturated, linear or branched group, which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a single bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a single bond, including, for example and not restricted to, vinyl, oleyl, linoleyl and similar groups.

The term "alkynyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more triple carbon-carbon bonds, preferably 1, 2 or 3 triple carbon-carbon bonds, conjugated or unconjugated, which is bound to the rest of the molecule by a single bond, including, for example and not restricted to, the ethynyl group, 1-propinyl, 2-propinyl, 1-butinyl, 2-butinyl, 3-butinyl, pentinyl, such as 1-pentinyl, and similar.

The term "alycyclyl group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably between 3, 4, 5 or 6 carbon atoms and which is bound to the rest of the molecule by a single bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, and which is bound to the rest of the molecule by a single bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, and which is bound to the rest of the molecule by a single bond, including, for example and not restricted to, the cyclooct-2-in-1-yl group and similar.

The term "aryl group" refers to an aromatic group which has between 6 and 30, preferably between 6 and 18, more preferably between 6 and 10, even more preferably between 6 or 10 carbon atoms, which comprises 1, 2, 3 or 4 aromatic rings, bound by a carbon-carbon bond or fused, including, for example and not restricted to, phenyl, naphthyl, diphenyl, indenyl, phenanthryl or antranyl, among others; or a aralkyl group.

The term "aralkyl group" refers to an alkyl group substituted by an aromatic group, with between 7 and 24 carbon atoms and including, for example and not restricted to, —$(CH_2)_{1-6}$-phenyl, —$(CH_2)_{1-6}$-(1-naphthyl), —$(CH_2)_{1-6}$-(2-naphthyl), —$(CH_2)_{1-6}$—CH(phenyl)$_2$ and similar.

The term "heterocyclyl group" refers to a hydrocarbonated ring of 3-10 members, in which one or more of the atoms in the ring, preferably 1, 2 or 3 of the atoms in the ring, is a different element to carbon, such as nitrogen, oxygen or sulfur and can be saturated or unsaturated. For the purposes of this invention, the heterocycle can be a monocyclic, bicyclic or tricyclic system, which can include systems of condensed rings; and the nitrogen, carbon or sulfur atoms can optionally be oxidized in the radical heterocyclyl; the nitrogen atom can optionally be quaternized; and the radical heterocyclyl can be partially or completely saturated or aromatic. The greatest preference is for the term heterocyclyl to refer to a ring of 5 or 6 members.

The term "heteroarylalkyl group" refers to an alkyl group substituted by a substituted or unsubstituted aromatic heterocyclyl group, the alkyl group having from 1 to 6 carbon atoms and the aromatic heterocyclyl between 2 and 24 carbon atoms and from 1 to 3 atoms other than carbon and including, for example and not restricted to, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As it is understood in this technical field, there can be a certain level of substitution of the aforementioned groups. Therefore, there can be substitution in any of the groups of this invention. The references in this document to substituted groups in the groups of this invention indicate that the specified radical can be substituted in one or more positions available by one or more substituents, preferably in 1, 2 or 3 positions, more preferably in 1 or 2 positions, yet more preferably in 1 position. These substituents include, for example and not restricted to, $C_1$-$C_4$ alkyl; hydroxyl; $C_1$-$C_4$ alcoxyl; amino; $C_1$-$C_4$ aminoalkyl; $C_1$-$C_4$ carbonyloxyl; $C_1$-$C_4$ oxycarbonyl; halogen such as fluoride, chlorine, bromine and iodine; cyano; nitro; azide; $C_1$-$C_4$ alkylsulfonyl; thiol; $C_1$-$C_4$ alkylthio; $C_6$-$C_{30}$ aryloxy such as phenoxyl; —$NR_b$ (C=$NR_b$)$NR_bR_c$; wherein $R_b$ and $R_c$ are independently selected from the group formed by H, $C_1$-$C_4$ alkyl, $C_2$-$C_4$ alkenyl, $C_2$-$C_4$ alkynyl, $C_3$-$C_{10}$ cycloalkyl, $C_6$-$C_{18}$ aryl, $C_7$-$C_{17}$ aralkyl, heterocyclyl of 3-10 members or protective group of the amino group.

Compounds of the Invention

The peptides of the invention are defined by the general formula (I)

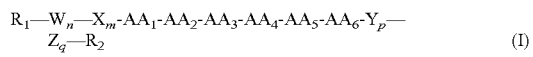

(I)

their stereoisomers, mixtures thereof and/or their cosmetically or pharmaceutically acceptable salts, wherein:

$AA_1$ is selected from the group formed by -Ser-, -Thr- and -Tyr-;

$AA_2$ is selected from the group formed by -Pro- and -Val-;

$AA_3$ is selected from the group formed by -Ala- and -Gly-;

$AA_4$ is selected from the group formed by -Glu-, -Gly- and -Val-;

$AA_5$ is selected from the group formed by -Gly- and -Ala-;

$AA_6$ is selected from the group formed by -Gln-, -Gly-, -His- and -Pro-;

W, X, Y, Z are amino acids and are independently selected from amongst themselves;

n, m, p and q are independently selected from amongst themselves and have a value of 0 or 1;

n+m+p+q is lower or equal to 2;

$R_1$ is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group formed by —$NR_3R_4$, —$OR_3$ and —$SR_3$, wherein $R_3$ and $R_4$ are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that $R_1$ and $R_2$ are not α-amino acids; when $AA_3$ is -Gly- and $AA_6$ is -Pro-, then $AA_2$ is -Val-; and when W or X are -Val-, Y or Z are -Arg-, $AA_1$ is -Ser-, $AA_2$ is -Pro-, $AA_4$ is -Glu-, $AA_5$ is -Ala- and $AA_6$ is -Gln-, then $AA_3$ is -Gly-.

Groups $R_1$ and $R_2$ are respectively bound to the amino-terminal (N-terminal) and carboxy-terminal (C-terminal) of the peptide sequences.

In accordance with a preferred embodiment of this invention $R_1$ is selected from the group formed by H or $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon and an alkyl chain of 1 to 6 carbon atoms. More preferably, $R_1$ is selected from H, acetyl, tert-butanoyl, hexanoyl, 2-methylhexanoyl, cyclohexenecarboxyl, octanoyl, decanoyl, lauroyl myristoyl, palmitoyl, stearoyl, oleoyl and linoleoyl. Even more preferably, $R_1$ is H, acetyl, lauroyl, myristoyl or palmitoyl. In an even more preferred embodiment, $R_1$ is acetyl or palmitoyl.

In accordance with another preferred embodiment, $R_2$ is —$NR_3R_4$, —$OR_3$ or —$SR_3$ wherein $R_3$ and $R_4$ are independently selected from the group formed by H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$, wherein $R_3$ and $R_4$ are independently selected from the group formed by H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and substituted or unsubstituted heterocyclyl of 3-10 members, substituted or unsubstituted heteroarylalkyl with a ring of 3 to 10 members and an alkyl chain of 1 to 6 carbon atoms. More preferably $R_3$ and $R_4$ are selected from the group formed by H, methyl, ethyl, hexyl, dodecyl, or hexadecyl. Even more preferably $R_3$ is H and $R_4$ is selected from the group formed by H, methyl, ethyl, hexyl, dodecyl, or hexadecyl. In accordance with an even more preferred embodiment, $R_2$ is selected from —OH and —$NH_2$.

In accordance with another embodiment of this invention $R_1$ is selected from the group formed by H, acetyl, lauroyl, myristoyl or palmitoyl, $AA_1$ is -L-Tyr-, $AA_2$ is -L-Pro-, $AA_3$ is -L-Ala-, $AA_4$ is -L-Glu-, $AA_5$ is -L-Gly-, $AA_6$ is -L-Gln-, and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl or palmitoyl, $AA_1$ is -L-Ser-, $AA_2$ is -L-Val-, $AA_3$ is -L-Ala-, $AA_4$ is -L-Val-, $AA_5$ is -L-Gly-, $AA_6$ is -L-Gln- and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl or palmitoyl, $AA_1$ is -L-Ser-, $AA_2$ is -L-Pro-, $AA_3$ is -L-Ala-, $AA_4$ is -L-Gly-, $AA_5$ is -L-Gly-, $AA_6$ is -L-Pro-, and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl and palmitoyl, preferably $R_1$ is selected from the group formed by H, acetyl, lauroyl, myristoyl and palmitoyl and $R_2$ is selected from the group formed by —OH and —$NH_2$.

In accordance with another embodiment of this invention n, m, p and q are 0.

Preferably, the peptides in formula (I) are selected from the group formed by:

```
Ac-Ala-Ser-Pro-Ala-Gly-Gly-Pro-NH2
(Ac-SEQ ID 1-NH2)

Ac-Gly-Ser-Pro-Ala-Gly-Gly-Pro-Gly-NH2
(Ac-SEQ ID 2-NH2)

Ac-Ile-Ser-Val-Ala-Gly-Gly-Gly-Ala-NH2
(Ac-SEQ ID 3-NH2)

Ac-Ile-Ser-Val-Ala-Gly-Gly-His-NH2
(Ac-SEQ ID 4-NH2)

Ac-Ser-Pro-Ala-Glu-Gly-Gln-NH2
(Ac-SEQ ID 5-NH2)

Ac-Ser-Pro-Ala-Glu-Gly-Gly-NH2
(Ac-SEQ ID 6-NH2)

Ac-Ser-Pro-Ala-Gly-Gly-Gln-Ala-NH2
(Ac-SEQ ID 7-NH2)

Ac-Ser-Pro-Ala-Gly-Gly-Gln-NH2
(Ac-SEQ ID 8-NH2)

Ac-Ser-Pro-Ala-Gly-Gly-Pro-Gly-NH2
(Ac-SEQ ID 9-NH2)

Ac-Ser-Pro-Ala-Gly-Gly-Pro-NH-(CH2)15-CH3
(Ac-SEQ ID 10-NH-(CH2)15-CH3)

Ac-Ser-Pro-Ala-Gly-Gly-Pro-NH2
(Ac-SEQ ID 10-NH2)

Ac-Ser-Pro-Ala-Gly-Gly-Pro-OH
(Ac-SEQ ID 10-OH)

Ac-Ser-Pro-Ala-Val-Ala-Gly-Gly-Ala-NH2
(Ac-SEQ ID 11-NH2)

Ac-Ser-Val-Ala-Glu-Gly-Gln-NH2
(Ac-SEQ ID 12-NH2)

Ac-Ser-Val-Ala-Gly-Gly-Pro-NH2
(Ac-SEQ ID 13-NH2)

Ac-Ser-Val-Ala-Val-Ala-Gln-OH
(Ac-SEQ ID 14-NH2)

Ac-Ser-Val-Ala-Val-Gly-Gln-NH-(CH2)15-CH3
(Ac-SEQ ID 15-NH-(CH2)15-CH3)

Ac-Ser-Val-Ala-Val-Gly-Gln-NH2
(Ac-SEQ ID 15-NH2)

Ac-Ser-Val-Ala-Val-Gly-Gln-OH
(Ac-SEQ ID 15-OH)

Ac-Ser-Val-Ala-Val-Gly-Gly-NH2
(Ac-SEQ ID 16-NH2)

Ac-Ser-Val-Ala-Val-Gly-Pro-NH2
(Ac-SEQ ID 17-NH2)

Ac-Ser-Val-Gly-Glu-Gly-His-NH2
(Ac-SEQ ID 18-NH2)

Ac-Ser-Val-Gly-Val-Gly-Gln-OH
(Ac-SEQ ID 19-OH)

Ac-Thr-Pro-Ala-Gly-Gly-Pro-NH2
(Ac-SEQ ID 20-NH2)

Ac-Thr-Pro-Gly-Gly-Gly-Pro-NH2
(Ac-SEQ ID 21-NH2)

Ac-Tyr-Pro-Ala-Glu-Gly-Gln-NH-(CH2)15-CH3
(Ac-SEQ ID 22-NH-(CH2)15-CH3)

Ac-Tyr-Pro-Ala-Glu-Gly-Gln-NH2
(Ac-SEQ ID 22-NH2)

Ac-Tyr-Pro-Ala-Glu-Gly-Gln-OH
(Ac-SEQ ID 22-OH)

Ac-Tyr-Pro-Ala-Glu-Gly-Gly-NH2
(Ac-SEQ ID 23-NH2)

Ac-Tyr-Pro-Ala-Glu-Gly-Pro-NH2
(Ac-SEQ ID 24-NH2)

Ac-Tyr-Pro-Ala-Gly-Gly-Gly-NH2
(Ac-SEQ ID 25-NH2)

Ac-Tyr-Pro-Ala-Gly-Gly-Pro-NH2
(Ac-SEQ ID 26-NH2)

Ac-Tyr-Pro-Ala-Gly-Gly-Val-NH2
(Ac-SEQ ID 27-NH2)

Ac-Tyr-Pro-Ala-Val-Gly-Gln-NH2
(Ac-SEQ ID 28-NH2)

Ac-Tyr-Pro-Ala-Val-Gly-Gly-NH2
(Ac-SEQ ID 29-NH2)

Ac-Tyr-Pro-Ala-Val-Gly-His-NH2
(Ac-SEQ ID 30-NH2)

Ac-Tyr-Pro-Ala-Val-Gly-Pro-NH2
(Ac-SEQ ID 31-NH2)

Ac-Tyr-Val-Ala-Glu-Gly-Pro-NH2
(Ac-SEQ ID 32-NH2)

Ac-Tyr-Val-Ala-Gly-Gly-Gly-NH2
(Ac-SEQ ID 33-NH2)

Ac-Tyr-Val-Ala-Gly-Gly-His-NH2
(Ac-SEQ ID 34-NH2)

Ac-Tyr-Val-Ala-Gly-Gly-Pro-NH2
(Ac-SEQ ID 35-NH2)

Ac-Tyr-Val-Ala-Val-Gly-Gly-NH2
(Ac-SEQ ID 36-NH2)

Ac-Val-Ser-Pro-Ala-Val-Gly-Gln-NH2
(Ac-SEQ ID 37-NH2)

Palm-Ser-Pro-Ala-Gly-Gly-Pro-NH2
(Palm-SEQ ID 10-NH2)

Palm-Ser-Pro-Ala-Gly-Gly-Pro-OH
(Palm-SEQ ID 10-OH)

Palm-Ser-Val-Ala-Val-Gly-Gln-NH2
(Palm-SEQ ID 15-NH2)

Palm-Ser-Val-Ala-Val-Gly-Gln-OH
(Palm-SEQ ID 15-OH)
```

```
-continued
Palm-Tyr-Pro-Ala-Glu-Gly-Gln-NH2
(Palm-SEQ ID 22-NH2)

Palm-Tyr-Pro-Ala-Glu-Gly-Gln-OH
(Palm-SEQ ID 22-OH)
``` their stereoisomers, mixtures thereof and/or their cosmetically or pharmaceutically acceptable salts.

The peptides of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the peptides of the invention are pure isomers, i.e., enantiomers or diastereomers.

For example, when it is stated that $AA_1$ can be Ser-, it is understood that $AA_1$ is selected from -L-Ser-, -D-Ser- or mixtures of both, racemic or non-racemic. In the same way, when it is said that $AA_2$ can be -Pro-, it is understood that it can be -L-Pro-, -D-Pro- or mixtures of both, racemic or non-racemic. The preparation processes described in this document enable the person skilled in the art to obtain each of the stereoisomers of the peptide of the invention by choosing the amino acid with the right configuration.

In the context of this invention, the term "amino acids" includes the amino acids codified by the genetic code as well as uncodified amino acids, either they are natural or not. Examples of non-codified amino acids are, without restriction, citrulline, ornithine, sarcosine, desmosine, norvaline, 4-aminobutyric acid, 2-aminobutyric acid, 2-aminoisobutyric acid, 6-aminohexanoyc acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, a amino acids and β amino acids, among others, as well as their derivatives. A list of unnatural amino acids can be found in the article "Unusual amino acids in peptide synthesis" by D. C. Roberts and F. Vellaccio, in The Peptides, Vol. 5 (1983), Chapter VI, Gross E. and Meienhofer J., Eds., Academic Press, New York, USA or in the commercial catalogues of the companies specialized in the field.

In the context of this invention, when n, m, p or q are not 0 it is clearly understood that the nature of W, X, Y and/or Z does not hinder the activity of the peptides of the invention, but that it contributes to the modulation of AQP-3 and/or stimulation of collagen synthesis or has no effect on them.

The cosmetically and pharmaceutically acceptable salts of the peptides provided by this invention are also found within the field of this invention. The term "cosmetically or pharmaceutically acceptable salts" means a salt recognized for its use in animals and more specifically in human beings, and includes salts used to form base addition salts, either they are inorganic, such as and not restricted to, lithium, sodium, potassium, calcium, magnesium, manganese, copper, zinc or aluminium among others, either they are organic, such as and not restricted to, ethylamine, diethylamine, ethylenediamine, ethanolamine, diethanolamine, arginine, lysine, histidine or piperazine among others, or acid addition salts, either they are organic, such as and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, such as and not restricted to, chloride, sulfate, borate or carbonate, among others. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al., "*Pharmaceutical Salts*", *J. Pharm. Sci.*, (1977), 66, 1-19].

Another aspect of this invention relates to a peptide of general formula (I), its stereoisomers, mixtures thereof and/or its cosmetically or pharmaceutically acceptable salts, as described in this invention, for its use in the treatment and/or care of the skin and/or mucous membranes.

In another particular aspect, this invention relates to a peptide of general formula (I), its stereoisomers, mixtures thereof and/or its cosmetically or pharmaceutically acceptable salts, as described in this invention, for its use in the modulation of AQP-3.

In another particular aspect, this invention relates to a peptide of general formula (I), its stereoisomers, mixtures thereof and/or its cosmetically or pharmaceutically acceptable salts, as described in this invention, for its use in the stimulation of collagen synthesis.

In another particular aspect, this invention relates to a peptide of general formula (I), its stereoisomers, mixtures thereof and/or its cosmetically or pharmaceutically acceptable salts, as described in this invention, for its use in the hydration of the skin and/or mucous membranes.

An aspect of this invention relates to a peptide of general formula (I), its stereoisomers, mixtures thereof and/or its cosmetically or pharmaceutically acceptable salts, as described in this invention, to improve the skin barrier function.

An aspect of this invention relates to a peptide of general formula (I), its stereoisomers, mixtures thereof and/or its cosmetically or pharmaceutically acceptable salts, as described in this invention, for its use in reepithelization and/or healing of the skin and/or mucous membranes.

An aspect of this invention relates to a peptide of general formula (I), its stereoisomers, mixtures thereof and/or its cosmetically or pharmaceutically acceptable salts, as described in this invention, for its use in the treatment and/or prevention of aging and/or photoaging of the skin.

An aspect of this invention refers to a peptide of general formula (I), its stereoisomers, mixtures thereof and/or its cosmetically or pharmaceutically acceptable salts, as described in this invention, for its use in the treatment and/or reduction of facial wrinkles.

In another particular aspect, this invention refers to a peptide of general formula (I), its stereoisomers, mixtures thereof and/or its cosmetically or pharmaceutically acceptable salts, as described in this invention, for its use in the treatment and/or care of those conditions, disorders and/or diseases of the skin and/or mucous membranes selected from the group formed by diseases and/or disorders of the skin and/or mucous membranes related to inefficient or abnormal transportation of water in epidermis, psoriasis, dermatitis, atopic dermatitis, allergic dermatitis, eczema, spongiosis, edema, hereditary ichthyosis, senile xerosis, vaginal dryness, palmar hyperkeratosis, plantar hyperkeratosis, wrinkles, expression wrinkles, stretch marks, aged skin, photoaged skin, skin cancer, healing or reepithelization disorders, chronic ulcers, acne, keloids, hypertrophic scars, cellulitis, orange peel skin, elastosis, actinic elastosis, keratosis, rosacea, telangiectasia, couperosis, bags under the eyes, periorbital dark circles, varicose veins, alopecia, gingivitis, periodontitis, inflammatory processes and bullous pemphigoid.

In another particular aspect, the treatment and/or care of this invention is carried out by topical or transdermal application, preferably, the topical or transdermal application is carried out by iontophoresis, sonophoresis, electroporation, mechanical pressure, osmotic pressure gradient, occlusive cure, microinjections, by needle-free injections by means of pressure, by microelectric patches or any combination thereof.

In another particular aspect, the treatment and/or care is carried out by oral administration.

Preparation Processes

Synthesis of the peptides of the invention, their stereoisomers or their cosmetically or pharmaceutically acceptable salts can be carried out according to conventional methods, known in the prior art, such as using solid phase peptide synthesis methods [Stewart J. M. and Young J. D., "*Solid Phase Peptide Synthesis, 2nd edition*", (1984), Pierce Chemical Company, Rockford, Ill.; Bodanzsky M., Bodanzsky A. "*The practice of Peptide Synthesis*", (1984), Springer Verlag, New Cork; Lloyd-Williams P., Albericio F., Giralt E. "*Chemical Approaches to the Synthesis of Peptides and Proteins*", (1997), CRC, Boca Raton, Fla., USA], synthesis in solution, a combination of the methods of solid phase synthesis and synthesis in solution or enzymatic synthesis [Kullmann W., "*Proteases as catalysts for enzymic syntheses of opioid peptides*", (1980), *J. Biol. Chem.*, 255, 8234-8238]. Peptides can also be made by biotechnological processes with the aim of producing the desired sequences, or by controlled hydrolysis of proteins with animal, fungal, or preferably plant origins, which free peptide fragments which contain, at least, the desired sequence.

For example, a method of obtaining the peptides of the invention of formula (I) comprises the stages of:
- coupling of an amino acid, with the N-terminal end protected and the C-terminal end free, with an amino acid with the N-terminal end free and the C-terminal end protected or bound to a solid carrier;
- elimination of the group protecting the N-terminal end;
- repetition of the coupling sequence and elimination of the group protecting the N-terminal end until the desired peptide sequence is obtained;
- elimination of the group protecting the C-terminal end or cleavage of the solid carrier.

Preferably, the C-terminal end is bound to a solid carrier and the process is carried out in solid phase and, therefore, comprises the coupling of an amino acid with the protected N-terminal end and the free C-terminal end with an amino acid with the N-terminal end free and the C-terminal end bound to a polymer carrier; elimination of the group protecting the N-terminal end; and repetition of this sequence as many times as is necessary to thus obtain the peptide of the desired length, finally followed by the cleavage of the synthesized peptide of the original polymeric carrier.

The functional groups of the side chains of the amino acids are maintained conveniently protected with temporary or permanent protective groups throughout synthesis, and can be unprotected simultaneously or orthogonally to the process of cleavage of the peptide of the polymeric carrier.

Alternatively, solid phase synthesis can be carried out using a convergent strategy coupling a peptide with the polymeric carrier or with an amino acid previously bound to the polymeric carrier. Convergent synthesis strategies are widely known by persons skilled in the art and are described in Lloyd-Williams P. et al, "*Convergent solid-phase peptide synthesis*", (1993), *Tetrahedron*, 49, 11065-11133.

The process can comprise the additional stages of the N-terminal and C-terminal ends deprotection and/or cleavage of the peptide of the polymeric carrier in an indiscriminant order, using standard processes and conditions known in the prior art, after which the functional groups of these ends can be modified. The optional modification of the N-terminal and C-terminal ends can be carried out with the peptide of formula (I) anchored to the polymeric carrier or once the peptide has been separated from the polymeric carrier.

Optionally, $R_1$ can be introduced by the reaction of the N-terminal end of the peptide of the invention with a $R_1$—X compound, wherein $R_1$ has the aforementioned meaning and X is a leaving group, such as and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric carrier.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (CIZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-di nitrophenyl (Dnp), N-[1-(4,4-dimethyl-2,6-dioxacyclohex-1-ylidene)ethyl (Dde), 1-(4,4-dimethyl-2,6-dioxo-cyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3- methylbutyl]amino)benzyl ester (Dmab), among others; preferred protective groups of the invention are the All, tBu, cHx, Bzl and Trt esters.

The side chains of the trifunctional amino acids can be protected during the synthetic process with temporary or permanent protective groups orthogonal to the protective groups of the N-terminal and C-terminal ends.

The hydroxyl group of the tyrosine side chain can be protected with the 2-bromobenzyloxycarbonyl group (2-BrZ), tert-butyl (tBu), allyl (All), benzyl (Bzl) or 2,6-dichlorobenzyl (2,6-diClZ) among others. The threonine and serine side chains can be protected by a protective group selected from the group formed by tBu, Bzl, Trt and Ac. The histidine side chain is protected by a protective group selected from the group formed by Tos, Dnp, methyl (Me), Boc, benzyloxymethyl (Bom), Bzl, Fmoc, Mts, Trt and Mtt. The amide group of the glutamine side chain can be protected by the trityl group (Trt) or the xanthyl group (Xan) or can be used unprotected. For the protection of the carboxyl group of the glutamic acid side chain esters can be used such as tert-butyl ester (tBu), allyl ester (All), triphenylmethyl ester (trityl ester, Trt), cyclohexyl ester (cHx), benzyl ester (Bzl), orto-nitrobenzyl ester, para-nitrobenzyl ester, para-methoxybenzyl ester, trimethylsilylethyl ester, 2-phenylisopropyl ester, fluorenylmethyl ester (Fm) or 4-(N-[1-(4,4-dimethyl-2,6-dioxocyclohexylidene)-3-methylbutyl]amino)benzyl ester (Dmab), among others.

In a preferred embodiment, the protective group strategy used is the strategy wherein the amino groups are protected by Boc, the carboxyl groups are protected by Bzl, cHx or All, the tyrosine side chain is protected with 2-BrZ or Bzl, the serine and threonine side chains are protected by the Bzl group, the histidine side chain is protected by the Tos or Born group, the glutamic acid side chain is protected by Bzl, cHx or All, and glutamine is used unprotected in its side chain.

In another preferred embodiment, the protective group strategy used is the strategy wherein the amino groups are protected by Fmoc, the carboxyl groups are protected by tBu, All or Trt, the tyrosine side chain is protected by tBu and the serine and threonine side chains are protected by the tBu group, the histidine side chain is protected by the Trt or Mtt group, the glutamic acid side chain is protected by tBu or All, and glutamine is used protected by the Trt group in its side chain.

Examples of these and other additional protective groups, their introduction and removal, can be found in the literature [Atherton B. and Sheppard R. C., "*Solid Phase Peptide Synthesis: A practical approach*", (1989), IRL Oxford University Press]. The term "protective groups" also includes the polymeric carriers used in solid phase synthesis.

When synthesis takes place totally or partially in solid phase, the possible solid carriers used in the process of the invention involve polystyrene carriers, polyethylene glycol grafted to polystyrene and similar, such as and not restricted to, p-methylbenzhydrylamine resins (MBHA) [Matsueda G. R. et al, "*A p-methylbenzhydrylamine resin for improved solid-phase synthesis of peptide amides*". Peptides, (1981), 2, 45-50], 2-chlorotrityl resins [Barlos K. et al., "*Darstellung geschützter Peptid-Fragmente unter Einsatz substituierter Triphenylmethyl-Harze*". Tetrahedron Lett., (1989), 30, 3943-3946; Barlos K. et al., "*Veresterung von partiell geschützten Peptid-Fragmenten mit Harzen. Einsatz von 2-Chlorotritylchlorid zur Synthese von Leu1-Gastrin I*". Tetrahedron Lett., (1989), 30, 3947-3951], TentaGel® resins (Rapp Polymere GmbH), ChemMatrix® resins (Matrix Innovation, Inc) and similar, which may or may not include a labile linker, such as 5-(4-aminomethyl-3,5-dimethoxyphenoxy) valeric acid (PAL) [Albericio F. et al., "*Preparation and application of the 5-(4-(9-fluorenylmethyloxycarbonyl) aminomethyl-3,5-dimethoxy-phenoxy)valeric acid (PAL) handle for the solid-phase synthesis of C-terminal peptide amides under mild conditions*". J. Org. Chem., (1990), 55, 3730-3743], 2-(AM) [Rink H., "*Solid-phase synthesis of protected peptide fragments using a trialkoxy-diphenyl-methylester resin*". Tetrahedron Lett., (1987), 28, 3787-3790], Wang [Wang S. S., "*p-Alkoxybenzyl Alcohol Resin and p-Alkoxybenzyloxycarbonylhydrazide Resin for Solid Phase Synthesis of Protected Peptide Fragments.*" J. Am. Chem. Soc., (1973), 95, 1328-1333] and similar, which enable simultaneous deprotection and cleavage of the peptide from the polymeric carrier.

Cosmetic or Pharmaceutical Compositions of the Invention

The peptides of the invention can be administered to modulate AQP-3 and/or stimulate collagen synthesis by any means which causes contact between the peptides and the site of action in a mammal's body, preferably that of a human being, and in the form of a composition which contains them.

In this regard, another aspect of the invention is a cosmetic or pharmaceutical composition which comprises at least one peptide of general formula (I), its stereoisomers, mixtures thereof, and/or its cosmetically or pharmaceutically acceptable salts together with at least one cosmetically or pharmaceutically acceptable adjuvant. These compositions can be prepared by conventional means known to persons skilled in the art ["*Harry's Cosmeticology*", Seventh edition, (1982), Wilkinson J. B., Moore R. J., ed. Longman House, Essex, GB].

The peptides of this invention have variable solubility in water, according to the nature of their sequence or any possible modifications in the N-terminal and/or C-terminal ends. Therefore, the peptides of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerine, butylene glycol or polyethylene glycol or any combination thereof.

The cosmetically or pharmaceutically effective amount of the peptides of the invention which should be administered, as well as their dosage, will depend on numerous factors, including age, state of the patient, the nature or severity of the condition, disorder or disease to be treated and/or cared for, the route and frequency of administration and of the particular nature of the peptides to be used.

"Cosmetically and pharmaceutically effective amount" is understood to mean a non-toxic but sufficient amount of the peptide or peptides of the invention to provide the desired effect. The peptides of the invention are used in the cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight).

The peptides of the invention or their functionally equivalent variants, their stereoisomers, mixtures thereof and/or their cosmetically or pharmaceutically acceptable salts, can also be incorporated into cosmetic or pharmaceutical delivery and/or sustained release systems.

The term "delivery systems" relates to a diluent, adjuvant, excipient or carrier with which the peptide of the invention is administered. These cosmetic or pharmaceutical carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents which can be used in the different delivery systems in which the peptide of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, millicapsules, microcapsules, nanocapsules, nanostructured lipid carriers, sponges, cyclodextrins, vesicles, micelles, mixed micelles of surfactants, surfactant-phospholipid mixed micelles, millispheres, microspheres, nanospheres, liposphere, microemulsions, nanoemulsions, miniparticles, milliparticles, microparticles, nanoparticles and solid lipid nanoparticles, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, nanocapsules containing microemulsions and microemulsions, more preferably water-in-oil microemulsions with an internal structure of reverse micelle.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal, subcutaneous implantation or injection, or direct implantation or injection into a specific body part, and preferably should release a relatively constant quantity of the peptides of the invention. The amount of peptide contained in the sustained release system will depend, for example, on where the composition is to be administered, the kinetics and duration of the release of the peptide of the invention, as well as the nature of the condition, disorder and/or disease to be treated and/or cared for.

The peptides of this invention can also be adsorbed on solid organic polymers or solid mineral supports such as and not restricted to, talc, bentonite, silica, starch or maltodextrin among others.

The compositions which contain the peptides of the invention, their stereoisomers, mixtures thereof and/or their cosmetically or pharmaceutically acceptable salts can also be incorporated into fabrics, non-woven fabrics and medical devices which are in direct contact with the skin, thus releasing the peptides of the invention either by biodegradation of the binding system to the fabric, non-woven fabric or medical device, or by friction between them and the body, due to bodily moisture, the skin's pH or body temperature. Furthermore, the peptides of the invention can be incorporated into the fabrics and non-woven fabrics used to make garments that are in direct contact with the body. Preferably, the fabrics, non-woven fabrics and medical devices containing the peptides of the invention are used for the treatment and/or care of conditions, disorders and/or diseases of the skin and/or mucous membranes which improve or are prevented by modulation of AQP-3 and/or by stimulation of collagen synthesis.

Examples of fabrics, non-woven fabrics, garments, medical devices and means for immobilizing the peptides to them, among which are the delivery systems and/or the sustained release systems described above, can be found in literature and are known in the prior art [Schaab C. K. "*Impregnating Fabrics With Microcapsules*", (1986), HAPPI May 1986; Nelson G. "*Application of microencapsulation in textiles*". *Int. J. Pharm.*, (2002), 242, 55-62; *"Biofunctional Textiles and the Skin"*. *Curr. Probl. Dermatol.*, (2006), v. 33; Hipler U. C. and Elsner P., eds. S. Karger A G, Basel, Switzerland; Malcom R. K.; McCullagh S. D. et al., "*Controlled release of a model antibacterial drug from a novel self-lubricating silicone biomaterial*"., *J. Cont. Release*, (2004), 97, 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the peptides of this invention, their stereoisomers, mixtures thereof and/or their cosmetically or pharmaceutically acceptable salts, can be used in different types of compositions of topical, transdermal, oral or parenteral application, which optionally include cosmetically or pharmaceutically acceptable excipients necessary for formulating the desired administration form. A person skilled in the art knows the different excipients which can be used in the cosmetic or pharmaceutical compositions which contain the peptides of the invention.

The compositions of topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols, including leave-on and rinse-off formulations. These topical or transdermal application formulations can be incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip glosses and powders among others.

The cosmetic or pharmaceutical compositions of the invention may include agents which increase the percutaneous absorption of the peptides of this invention, such as and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the cosmetic compositions containing the peptides of this invention, their stereoisomers and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, powders, granules, chewing gum, solutions, suspensions, emulsions, syrups, elixirs, polysaccharide films, jellies or gelatins, and any other form known by the person skilled in the art. In particular, the peptides of the invention can be incorporated into any form of functional food or fortified food, such as and not restricted to, dietary bars or compact or non-compact powders. These powders can be dissolved in water, juices, soda, dairy products, soy derivatives or can be incorporated into dietary bars. The peptides of this invention can be formulated with common excipients and adjuvants for oral compositions or food supplements, such as and not restricted to, fat components, aqueous components, humectants, preservatives, texturizing agents, flavors, aromas, antioxidants and colorants common in the food industry.

Cosmetic or pharmaceutical compositions containing the peptides of the invention, their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, vaginal, urethral, rectal route, subcutaneous, intradermal, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the peptides of the invention can be administered.

Among the cosmetically or pharmaceutically acceptable adjuvants contained in the cosmetic or pharmaceutical compositions described in this invention are additional ingredients commonly used in compositions for the treatment and/or care of the skin and/or mucous membranes such as and not restricted to, other AQP-3 modulating agents, aquaporin modulating agents, proteins from the aquaporin family, other collagen synthesis stimulating agents, agents modulating PGC-1α synthesis, agents modulating the activity of PPARγ, agents which increase or reduce the triglyceride content of adipocytes, agents stimulating or delaying adipocyte differentiation, lipolytic agents or agents stimulating lipolysis, anti-cellulite agents, adipogenic agents, inhibitors of acetylcholine-receptor aggregation, agents inhibiting muscle contraction, anticholinergic agents, elastase inhibiting agents, matrix metalloproteinase inhibiting agents, melanin synthesis stimulating or inhibiting agents, whitening or depigmenting agents, propigmenting agents, self-tanning agents, anti-aging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners such as humectants, substances that retain moisture, alpha hydroxyacids, beta hydroxyacids, moisturizers, epidermal hydrolytic enzymes, vitamins, amino acids, proteins, pigments or colorants, dyes, biopolymers, gelling polymers, thickeners, surfactants, softening agents, binding agents, preservatives, anti-wrinkle agents, agents able to reduce or treat the bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, heat shock proteins, HSP70 synthesis stimulators, heat shock protein synthesis-stimulating agents, hyaluronic acid synthesis-stimulating agents, fibronectin synthesis-stimulating agents, sirtuin synthesis-stimulating agents, agents stimulating the synthesis of lipids and components of the stratum corneum, ceramides, fatty acids, agents that inhibit collagen degradation, agents that inhibit elastin degradation, agents that inhibit serine proteases such cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents that inhibit acetylcholinesterase, skin relaxant agents, glycosaminoglycan synthesis-stimulating agents, antihyperkeratosis agents, comedolytic agents, anti-psoriatic agents, anti-dermatitis agents, anti-eczema agents, DNA repair agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, antiperspirant agents, agents stimulating healing, coadjuvant healing agents, agents stimulating reepithelization, coadjuvant reepithelization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, perfumes, perfumes, chelating agents, plant extracts, essential oils, marine extracts, agents obtained from a biofermentation process, mineral salts, cell extracts, sunscreens and organic or mineral photoprotective agents active against ultraviolet A and/or B rays or mixtures thereof, provided that they are physically and chemically compatible with the rest of components in the composition and particularly with the peptides of general formula (I) contained in the composition of this invention. Likewise, the nature of these additional ingredients should not unacceptably alter the benefits of the peptides of this invention. The nature of these additional ingredients can be synthetic or natural, such as plant extracts, or come from a biotechnological process, or from a combination of a synthetic process and a biotechnological process. Additional examples can be found in "*CTFA International Cosmetic Ingredient Dictionary & Handbook*", *12th Edition*, (2008). In the context of this invention, biotechnological process is understood to be any process to produce the active ingredient, or part of it, in an organism, or in part of it.

In addition, the cosmetic or pharmaceutical composition of this invention can comprise a cosmetically or pharmaceutically effective quantity of at least one compound, oil or wax selected from the group of the cosmetic or pharmaceutical adjuvants formed by humectants, substances which retain moisture, moisturizers and emollients, such as and not restricted to, polyols and polyethers such as glycerin, ethylhexylglycerin, caprylyl glycol, pentylene glycol, butylene glycol, propylene glycol and its derivatives, triethylene glycol, polyethylene glycol, Glycereth-26, Sorbeth-30; panthenol; pyroglutamic acid and its salts or derivatives; amino acids, such as serine, proline, alanine, glutamate or arginine; ectoin and its derivatives; N-(2-hydroxyethyl)acetamide; pyrrolidone carboxylic acid (PCA); N-lauroyl-pyrrolidone carboxylic acid; N-lauroyl-L-lysine; N-alpha-benzoyl-L-arginine; urea; creatine; alpha- and beta-hydroxy acids such as lactic acid, glycolic acid, malic acid, citric acid, tartaric acid or salicylic acid, and its salts; polyglyceryl acrilate; sugars and polysaccharides, such as glucose, isomerate saccharide, sorbitol, pentaerythritol, inositol, xylitol, sorbitol, trehalose and its derivatives, sodium glucuronate, carrageenans (*Chondrus crispus*) or chitosan; glycosaminoglycans such as hyaluronic acid and its derivatives; aloe vera in any of its forms; honey; soluble collagen; lecithin and phosphatidylcholine; ceramides; cholesterol and its esters; tocopherol and its esters, such as tocopheryl acetate or tocopheryl linoleate; long chain alcohols such as cetearyl alcohol, stearic alcohol, cetyl alcohol, oleyl alcohol, isocetyl alcohol or octadecan-2-ol; long chain alcohol esters such as lauryl lactate, myristyl acetate or $C_{12}$-$C_{15}$ alkyl benzoates; fatty acids such as stearic acid, isostearic acid or palmytic acid; polyunsaturated fatty acids (PUFAs); sorbitans such as sorbitan distearate; glycerides such as glyceryl monoricinoleate, glyceryl monostearate, glyceryl stearate citrate or caprylic and capric acid triglyceride; saccharose esters such as saccharose palmitate or saccharose oleate; butylene glycol esters, such as dicaprylate and dicaprate; fatty acid esters such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2-ethylhexyl cocoate, decyl oleate, myristyl myristate; squalene; mink oil; lanolin and its derivatives; acetylated lanolin alcohols; silicone derivatives such as cyclomethicone, dimethicone or dimethylpolysiloxane; Antarcticine® [INCI: Pseudoalteromonas Ferment Extract], Xpertmoist™ [INCI: Glycerin, Pseudoalteromonas Ferment Extract, Xanthan Gum, Proline, Alanine, Serine, Ethylhexylglycerin, Caprylyl Glycol], Bodyfensine™ [INCI: Acetyl Dipeptide-3 Aminohexanoate], or Hyadisine™ [INCI: Pseudoalteromonas Ferment Extract] marketed by Lipotec; petrolatum; mineral oil; mineral and synthetic waxes; beeswax (cera alba); paraffin; or waxes and oils of plant origin such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose seed oil (*Rosa moschata*), wild soybean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*) among others, and/or mixtures thereof.

An additional aspect of this invention relates to a cosmetic or pharmaceutical composition containing a cosmetically or pharmaceutically effective amount of at least one peptide of the invention according to the general formula (I), its stereoisomers, mixtures thereof and/or its cosmetically or pharmaceutically acceptable salts, and also a cosmetically or pharmaceutically effective amount of at least one anti-wrinkle agent and/or anti-aging agent selected, without restriction, from the group formed by the extracts or hydrolyzed extracts of *Vitis vinifera, Rosa canina, Curcuma longa, Theobroma cacao, Ginkgo biloba, Leontopodium alpinum* or *Dunaliella salina* among others or as well as at least one synthetic compound or product of biotechnological origin which is an anti-wrinkle agent and/or anti-aging agent such as and not restricted to Matrixyl® [INCI: Palmitoyl Pentapeptide-4], Matrixyl 3000® [INCI: Palmitoyl Tetrapeptide-7, Palmitoyl Oligopeptide], Essenskin™ [INCI: calcium hydroxymethionine], Renovage [INCI: teprenone] or Dermaxyl® [INCI: Palmitoyl Oligopeptide] marketed by Sederma/Croda, Vialox® [INCI: Pentapeptide 3], Syn® Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum] or Preregen® [INCI: *Glycine soja* (Soybean) Protein, Oxido Reductases] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9] or DN AGE™ LS [INCI: *Cassia alata* leaf Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI: Acetyl Hexapeptide-30], Aldenine® [INCI: Hydrolized wheat protein, hydrolized soy protein, Tripeptide 1], Preventhelia™ [INCI: Diaminopropionoyl Tripeptide-33], Decorinyl® [INCI: Tripeptide-10 Citrulline], Trylagen® [INCI: Pseudoalteromonas Ferment Extract, Hydrolyzed Wheat Protein, Hydrolyzed Soy Protein, Tripeptide 10 Citrulline, Tripeptide 1], Eyeseryl® [INCI: Acetyl Tetrapeptide-5], Peptide AC29 [INCI; Acetyl Tripeptide-30 Citrulline], Relistase™ [INCI: Acetylarginyltriptophyl Diphenylglycine], Thermostressine® [INCI: Acetyl Tetrapeptide-22], Lipochroman 6 [INCI: Dimethylmethoxy Chromanol], Chromabright™ [INCI: Dimethylmethoxy Chromanyl Palmitate], Antarcticine® [INCI: Pseudoalteromonas Ferment Extract], dGlyage™ [INCI: Lysine HCl, Lecithin, Tripeptide-9 Citrulline], Vilastene™ [INCI: Lysine HCl, Lecithin, Tripeptide-10 Citrulline] or Hyadisine™ [INCI: Pseudoalteromonas Ferment Extract] marketed by Lipotec, Kollaren® [INCI: Tripeptide 1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract] or Quintescine™ IS [INCI: Dipeptide-4] marketed by Vincience/ISP, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI:

*Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: *Pyrus malus* Fruit Extract, *Glycine soja* Seed Extract] or Juvenesce [INCI: Ethoxydiglicol and Caprylic Triglycerid, Retinol, Ursolic Acid, Phytonadione, Ilomastat] marketed by Coletica/Engelhard/BASF, Ameliox [INCI: Carnosine, Tocopherol, *Silybum marianum* Fruit Extract] or PhytoCellTec *Malus* Domestica [INCI: *Malus domestics* Fruit Cell Culture] marketed by Mibelle Biochemistry, Bioxilift [INCI: *Pimpinella anisum* Extract] or SMS Anti-Wrinkle® [INCI: *Annona squamosa* Seed Extract] marketed by Silab, antagonists of the Ca$^{2+}$channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase or T4 endonuclease V, or chloride channel agonists among others, and/or mixtures thereof.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and, in addition, a cosmetically or pharmaceutically effective amount of at least one AQP-3 modulating agent, such as and not restricted to, the extracts or hydrolyzed extracts of *Punica granatum, Ajuga turkestanica, Centella asiatica, Phellodendron amurense, Bertholletia, Panax ginseng*, glyceryl glycosides, hexosyl glycerides and/or (hexosyl) hexosyl glycerides; cyclic AMP analogs; PKA- (adenylyl cyclase) activators; phosphodiesterase inhibitors, for example and not restricted to, caffeine or theophylline, inorganic salts, such as alkaline earth salts, alkali salts containing chloride, sulfate, hydrogen sulfate, phosphate, hydrogen phosphate, linear or cyclic olygophosphate, carbonate or bicarbonate anion, particularly sodium chloride, sodium bromide, sodium iodide, borax, sodium silicate, sodium carbonate, sodium phosphate, sodium hydrogen phosphate, sodium dihydrogen phosphate, potassium chloride, potassium iodide, lithium chloride, ammonium chloride, zinc chloride, aluminium sulphite, magnesium chloride, magnesium sulfate, salts from acids produced by the skin, such as sodium liponate, sodium citrate, ammonium lactate, sodium lactate, sodium bicarbonate, sodium citrate, sodium propionate; sugars of up to 600 g/mol, for example and not restricted to, sorbitol, manitol, sucrose, glucose; amino acids, for example and not restricted to, asparagine, glycine, alanine, vitamin A and its esters, in particular vitamin A palmitate and acetate; vitamin E and its esters, in particular vitamin E palmitate and acetate; vitamin C and its derivatives, in particular magnesium ascorbyl phosphate; xanthines, especially caffeine; asiatic acid, madecassic acid, madecassoside, ellagic acid, soy saponins, pure sea water, magnesium aspartate, manganese chloride, cyclic AMP, D-xylose, hyaluronic acid, calcium gluconate, isoflavones, ammonium glycyrrhizinate, corticosteroids, resveratrol or piceids among others, and/or mixtures thereof.

In addition, this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and, in addition, a cosmetically or pharmaceutically effective amount of at least one agent stimulating healing, coadjuvant healing agent and/or reepithelization agent, for example and not restricted to, extracts or hydrolyzed extracts of *Aristoloquia clematis, Centella asiatica, Rosa moschata, Echinacea angustifolia, Symphytum officinal, Equisetum arvense, Hypericum perforatum, Mimosa tenuiflora, Persea gratisima, Prunus africanum, Tormentilla erecta, Aloe vera*, Polyplant® Epithelizing [INCI: *Calendula officinalis, Hypericum perforatum, Chamomilla recutita, Rosmarinus officinalis*] marketed by Provital, Cytokinol® LS 9028 [INCI: Hydrolyzed Casein, Hydrolyzed Yeast Protein, Lysine HCl] marketed by Laboratories Sérobiologiques/Cognis o Deliner® [INCI: *Zea mays* (Corn) Kernel Extract] marketed by Coletica/Engelhard among others, and/or a cosmetically or pharmaceutically effective amount of at least one synthetic compound, extract or product from a biotechnological process which is an agent stimulating healing, coadjuvant healing agent and/or reepithelization agent, for example and not restricted to, allantoin, cadherins, integrins, selectins, hyaluronic acid receptors, immunoglobulins, fibroblast growth factors, connective tissue growth factors, platelet-derived growth factors, vascular endothelial growth factors, epidermal growth factors, insulin-like growth factors, keratinocyte growth factor, colony-stimulating factor, transforming growth factor beta, tumor necrosis factor-alpha, interferons, interleukins, matrix metalloproteinases, protein tyrosine phosphatase receptors, Antarcticine® [INCI: Pseudoalteromonas Ferment extract], Bodyfensine® [INCI: Acetyl Dipeptide-3 Aminohexanoate] or Decorinyl™ [INCI: Tripeptide 10 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Xpertmoist™ [INCI: Glycerin, Pseudoalteromonas Ferment Extract, Xanthan Gum, Proline, Alanine, Serine, Ethylhexylglycerin, Caprylyl Glycol], Serilesine® [INCI: Hexapeptide-10] or Thermostressine™ [INCI: Acetyl Tetrapeptide-22], marketed by Lipotec, among others, and/or mixtures thereof.

An additional aspect of this invention relates to a cosmetic or pharmaceutical composition containing a cosmetically or pharmaceutically effective amount of at least one peptide of the invention according to the general formula (I), its stereoisomers, mixtures thereof and/or its cosmetically or pharmaceutically acceptable salts, and also a cosmetically or pharmaceutically effective amount of at least one anti-psoriasis, anti-dermatitis and/or anti-eczema agent, for example and not restricted to, corticosteroids, such as chlobetasol, betametasone, dexamethasone, halobetasol, diflorasone, fluocinonide, halcinonide, amcinonide, desoxymethasone, triamcinolone acetonide, mometasone, fluticasone, fluocinolone acetonide, flurandrenolide, desonide, prednicarbate, hidrocortisone, calcipotriene, vitamin D, anthralin, calcitriol, salicylic acid; coal tar, derivatives and sub-products of the coal industry; tar, derivatives and sub-products of petroleum distillation, tazarotene, antibiotics, azathioprine, colchicine, 5-fluorouracil, fumaric acid esters, hydroxyurea, mycophenolate mofetil, propylthiouracil, sulfasalazine, 6-thioguanine, calcineurin inhibitors, for example and not restricted to, tacrolimus and pimecrolimus; or topically applied retinoids, for example and not excluding, tretinoin, among others and/or mixtures thereof.

Applications

An aspect of this invention relates to the use of at least one peptide of general formula (I), its stereoisomers, mixtures thereof and/or its cosmetically or pharmaceutically acceptable salts in the preparation of a cosmetic or pharmaceutical composition for the treatment and/or care of skin and/or mucous membranes.

In addition, another aspect of this invention relates to the use of at least one peptide of general formula (I), its stereoisomers, mixtures thereof and/or its cosmetically or pharmaceutically acceptable salts in the preparation of a cosmetic or pharmaceutical composition for AQP-3 modulation.

In addition, another aspect of this invention relates to the use of at least one peptide of general formula (I), its stereoisomers, mixtures thereof and/or its cosmetically or pharmaceutically acceptable salts in the preparation of a cosmetic or pharmaceutical composition for collagen synthesis stimulation.

Another particular aspect of this invention relates to the use of at least one peptide of general formula (I), its stereoisomers, mixtures thereof and/or its cosmetically or pharmaceutically acceptable salts in the preparation of a cosmetic or pharmaceutical composition for the hydration of the skin and/or mucous membranes.

An aspect of this invention relates to the use of at least one peptide of general formula (I), its stereoisomers, mixtures thereof and/or its cosmetically or pharmaceutically acceptable salts in the preparation of a cosmetic or pharmaceutical composition to improve the skin barrier function.

An aspect of this invention relates to the use of at least one peptide of general formula (I), its stereoisomers, mixtures thereof and/or its cosmetically or pharmaceutically acceptable salts in the preparation of a cosmetic or pharmaceutical composition for the reepithelization and/or healing of the skin and/or mucous membranes.

An aspect of this invention relates to the use of at least one peptide of general formula (I), its stereoisomers, mixtures thereof and/or its cosmetically or pharmaceutically acceptable salts in the preparation of a cosmetic or pharmaceutical composition for the treatment and/or care of the skin's aging and/or photoaging.

Another aspect of this invention relates to the use of at least one peptide of general formula (I), its stereoisomers, mixtures thereof and/or its cosmetically or pharmaceutically acceptable salts in the preparation of a cosmetic or pharmaceutical composition for the treatment and/or reduction of facial wrinkles.

Another aspect of this invention relates to the use of at least one peptide of general formula (I), its stereoisomers, mixtures thereof and/or its cosmetically or pharmaceutically acceptable salts in the preparation of a cosmetic or pharmaceutical composition for the treatment and/or care of conditions, disorders and/or diseases of the skin and/or mucous membranes which improve or are prevented by AQP-3 modulation and/or by collagen synthesis stimulation selected from the group formed by diseases and/or disorders of the skin and/or mucous membranes related to inefficient or abnormal transportation of water in epidermis, psoriasis, dermatitis, atopic dermatitis, allergic dermatitis, eczema, spongiosis, edema, hereditary ichthyosis, senile xerosis, vaginal dryness, palmar hyperkeratosis, plantar hyperkeratosis, wrinkles, expression wrinkles, stretch marks, aged skin, photoaged skin, skin cancer, healing or reepithelization disorders, chronic ulcers, acne, keloids, hypertrophic scars, cellulitis, orange peel skin, elastosis, actinic elastosis, keratosis, rosacea, telangiectasia, couperosis, bags under the eyes, periorbital dark circles, varicose veins, alopecia, gingivitis, periodontitis, inflammatory processes and bullous pemphigoid.

In another aspect, the invention relates to a method for the treatment and/or care of the skin which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for the modulation of AQP-3 which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for collagen synthesis stimulation which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for hydration the skin and/or mucous membranes which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for improving the skin barrier function which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for reepithelization and/or healing of the skin and/or mucous membranes which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for treating and/or preventing aging and/or photoaging of the skin which comprises the administration of a cosmetically or pharmaceutically effective amount of at least one peptide of general formula (I), its stereoisomers, mixtures thereof and/or their cosmetically or pharmaceutically acceptable salts.

In another particular aspect, the treatment and/or prevention of aging and/or photoaging of the skin relates to a method for reducing and/or treating facial wrinkles.

In another particular aspect, this invention relates to a method for treating and/or caring for conditions, disorders and/or diseases of the skin and/or mucous membranes which improve or are prevented by AQP-3 modulation and/or by collagen synthesis stimulation selected from the group formed by diseases and/or disorders of the skin and/or mucous membranes related to inefficient or abnormal transportation of water in epidermis, psoriasis, dermatitis, atopic dermatitis, allergic dermatitis, eczema, spongiosis, edema, hereditary ichthyosis, senile xerosis, vaginal dryness, palmar hyperkeratosis, plantar hyperkeratosis, wrinkles, expression wrinkles, stretch marks, aged skin, photoaged skin, skin cancer, healing or reepithelization disorders, chronic ulcers, acne, keloids, hypertrophic scars, cellulitis, orange peel skin, elastosis, actinic elastosis, keratosis, rosacea, telangiectasia, couperosis, bags under the eyes, periorbital dark circles, varicose veins, alopecia, gingivitis, periodontitis, inflammatory processes and bullous pemphigoid, which comprises the administration of a cosmetically or pharmaceutically effective amount of at least one peptide of general formula (I), its stereoisomers, mixtures thereof and/or their cosmetically or pharmaceutically acceptable salts.

Examples of cosmetic or pharmaceutical compositions for the treatment and/or care of the skin and/or mucous membranes include creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, liniments, sera, soaps, serums, polysaccharide films, ointments, mousses, pomades, powders, bars, pencils and sprays or aerosols, including leave-on and rinse-off formulations, wipes, hydrogels, adhesive patches, non-adhesive patches, microelectric patches or face masks, make-up products such as make-up foundation, such as fluid foundations and compact foundations, make-up removal lotions, make-up removal milks, under-eye concealers, eye shadows, lipsticks, lip protectors, lip glosses and powders among others.

The compositions containing the peptides of this invention, their stereoisomers and/or their cosmetically or pharmaceutically acceptable salts can be applied to the skin and/or mucous membranes or be administered orally or parenterally as required to treat and/or care for a condition, disorder and/or disease.

The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day.

The following specific examples provided here illustrate the nature of this invention. These examples are included for illustrative purposes only and should not be construed as limitations on the invention claimed herein.

EXAMPLES

General Methodology

All reagents and solvents are of synthesis quality and are used without additional treatment.

Abbreviations

The abbreviations used for amino acids follow the 1983 IUPAC-IUB Joint Commission on Biochemical Nomenclature recommendations outlined in *Eur. J. Biochem.* (1984) 138:9-37.

®, resin; 2,6-diClZ, 2,6 dichlorobenzyl; 2-BrZ, 2-bromobenzyloxycarbonyl; 2-ClTrt-®, 2-chlorotrityl resin; Ac, acetyl; Adpoc, 1-(1-adamantyl)-1-methylethoxy-carbonyl; Ala, alanine; All, allyl; Alloc, allyloxycarbonyl; AM, 2-[4-aminomethyl-(2,4-dimethoxyphenyl)] phenoxyacetic acid; AQP-3, aquaporin-3; Arg, arginine; Boc, tert-butyloxycarbonyl; Bom, benzyloxymethyl; Bzl, benzyl; c.u., corneometric units; calcein-AM, acetomethoxy derivative of calcein; cAMP, cyclic adenosine monophosphate; Cbz, carboxybenzyl; cHx, cyclohexyl; ClZ, 2-chlorobenzyl; C-terminal, carboxy-terminal; DCM, dichloromethane; Dde, N-[1-(4,4-dimethyl-2,6-dioxocyclohex-1-ylidene)ethyl; DIEA, N,N'-diisopropylethylamine; DIPCDI, N,N'-diisopropylcarbodiimide; Dmab, 4-(N-[1-(4,4-dimethyl-2,6-dioxocyclohexylidene)-3-methylbutyl]amino)benzyl; DMEM, Dulbecco's Modified Eagle Medium; DMF, N,N-dimethylformamide; DNA, deoxyribonucleic acid; Dnp, 2,4-dinitrophenol; ELISA, Enzyme-linked immunosorbent assay; equiv, equivalent; ESI-MS, electrospray ionization mass spectrometry; FBS, fetal bovine serum; Fm, fluorenylmethyl; Fmoc, 9-fluorenylmethyloxycarbonyl; Glu, glutamic acid; Gln, glutamine; Gly, glycine; HDFa, Human Dermal Fibroblasts, adult; His, histidine; HOAt, 11-hydroxy-7-azabenzotriazole; HOBt, 1-hydroxybenzotriazole; HPLC, high performance liquid chromatography; HSP70, heat shock protein 70 kDa; INCI, International Nomenclature of Cosmetic Ingredients; ivDde, 1-(4,4-dimethyl-2,6-dioxocyclohexylidene)-3-methyl-butyl; MBHA, p-methylbenzhydrylamine; Me, methyl; MeCN, acetonitrile; MeOH, methanol; MMP, matrix metalloproteinases; mRNA, Messenger ribonucleic acid; Mts, mesitylenesulfonyl; Mtt, methoxytrityl or methyltrityl; NMF, natural moisturizing factor; N-terminal, amino terminal; PAL, 5-(4-aminomethyl-3,5-dimethoxyphenoxy) valeric acid; Palm, palmitoyl; PBS, phosphate buffered saline; PCA, pyrrolidone carboxylic acid; PCR, polymerase chain reaction; PGC-1α, PPARγ coactivator 1α; pNZ, p-nitrobenzyloxycarbonyl; PPARγ, peroxisome proliferator-activated receptor; Pro, proline; PUFAs, polyunsaturated fatty acids; q.s., quantity sufficient; q.s.p., quantity sufficient for; RNA, ribonucleic acid; Ser, serine; tBu, tert-butyl; Teoc, 2-(trimethylsilyl)ethyloxycarbonyl; TFA, trifluoroacetic acid; TGF-beta, transforming growth factor-beta; THF, tetrahydrofuran; TIS, triisopropylsilane; Tos, tosyl or p-toluenesulfonyl; Troc, 2,2,2 trichloroethoxycarbonyl; Trt, triphenylmethyl or trityl; Tyr, tyrosine; ULV, unilaminar vesicles; UVA, ultraviolet radiation A; UVB, ultraviolet radiation B; Val, valine; Xan, xanthyl; Z, benzyloxycarbonyl.

Chemical Synthesis

All synthetic processes were carried out in polypropylene syringes fitted with porous polyethylene discs. All the reagents and solvents were synthesis quality and were used without any additional treatment. The solvents and soluble reagents were removed by suction. The Fmoc group was removed with piperidine-DMF (2:8, v/v) (1×1 min, 1×5 min, 5 mL/g resin) [Lloyd-Williams P. et al. (1997) "*Chemical Approaches to the Synthesis of Peptides and Proteins*" CRC, Boca Raton (FL, USA)]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser E. et al., *Anal. Biochem.*, (1970), 34: 595-598] or chloranil test [Christensen T., *Acta Chem. Scand.*, (1979), 338: 763-766]. All synthetic reactions and washes were carried out at 25° C.

HPLC chromatographic analysis was carried out with Shimadzu equipment (Kyoto, Japan) using a reversed-phase column thermostatized at 30° C. (250×4.0 mm, Kromasil $C_8$, 5 μm, Akzo Nobel, Sweden). The elution was carried out using a gradient of acetonitrile (+0.07% TFA) in water (+0.1% TFA) at a flow rate of 1 mL/min and detection was carried out at 220 nm. The electrospray ionization mass spectrometry was carried out in a WATERS Alliance ZQ 2000 detector using a mixture of MeCN:$H_2O$ 4:1 (+0.1% TFA) as the mobile phase and a flow rate of 0.2 mL/min.

Example 1

Obtaining Fmoc-$W_n$—$X_m$-$AA_1$-$AA_2$-$AA_3$-$AA_4$-$AA_5$-$AA_6$-$Y_p$—$Z_q$—O-2-ClTrt-®, Wherein $AA_1$ is -L-Tyr- or -L-Ser-; $AA_2$ is -L-Pro- or -L-Val-; $AA_3$ is -L-Ala-; $AA_4$ is -L-Val-, -L-Glu- or -Gly-; $AA_5$ is -Gly-; $AA_6$ is -L-Pro-, -L-His-, -Gly- or -L-Gln-; and n, m, p and q are 0

5.37 g of Fmoc-L-Gln(Trt)-OH, 2.62 g of Fmoc-Gly-OH, 5.45 g of Fmoc-L-His(Trt)-OH, or 2.97 g of Fmoc-L-Pro-OH (8.8 mmol; 1 equiv) dissolved in 55 mL of DCM to which was added 1.3 mL of DIEA (7.6 mmol; 0.86 equiv) were coupled onto the dry 2-chlorotrityl resin (5.5 g; 8.8 mmol). They were stirred for 5 min, after which 2.5 mL of DIEA were added (14.6 mmol; 1.66 equiv). The mixture was allowed to react for 40 min. The remaining chloride groups were blocked by treatment with 4.4 mL of MeOH.

The N-terminal Fmoc group was deprotected as described in the general methods and 6.54 g of Fmoc-Gly-OH or 7.25 g of Fmoc-L-Ala-OH (22 mmol; 2.5 equiv) were coupled onto the peptidyl resins in the presence of DIPCDI (3.39 mL, 22 mmol, 2.5 equiv) and HOBt (3.37 g, 22 mmol, 2.5 equiv) using DMF as a solvent for 1 hour. The resins were then washed as described in the general methods and the deprotection treatment of the Fmoc group was repeated to couple the next amino acid. Following the protocols described 7.47 g of Fmoc-L-Val-OH, 6.54 g of Fmoc-Gly-OH or 9.76 g of Fmoc-L-Glu(OtBu)-OH (22 mmol; 2.5 equiv); 6.54 g of Fmoc-Gly-OH; 7.42 g of Fmoc-L-Pro-OH or 7.47 g of Fmoc-L-Val-OH (22 mmol; 2.5 equiv) and subsequently 10.11 g of Fmoc-L-Tyr(tBu)-OH, 8.74 g of Fmoc-L-Thr(tBu)-OH or 8.44 g of Fmoc-L-Ser(tBu)-OH (22 mmol; 2.5 equiv) were sequentially coupled in the presence of 3.37 g of HOBt (22 mmol; 2.5 equiv) and 3.39 mL of DIPCDI (22 mmol; 2.5 equiv) in each coupling.

After the synthesis, the peptidyl resins were washed with DCM (5×3 min) and dried by nitrogen stream.

Fmoc-$W_n$—$X_m$-$AA_1$-$AA_2$-$AA_3$-$AA_4$-$AA_5$-$AA_6$-$Y_p$—$Z_q$—O—2-ClTrt-®, wherein $AA_1$ is -L-Tyr-, -L-Thr- or -L-Ser-; $AA_2$ is -L-Pro- o -L-Val-; $AA_3$ is -L-Ala- or -L-Gly-; $AA_4$ is -L-Val-, -L-Glu- or -Gly-; $AA_5$ is -L-Ala- or -Gly-; $AA_6$ is -L-Pro-, -L-His-, -Gly- or -L-Gln-; and n, m, p and q are 0 could be similarly obtained.

Example 2 (Prophetic)

Obtaining Fmoc-$W_n$—$X_m$-$AA_1$-$AA_2$-$AA_3$-$AA_4$-$AA_5$-$AA_6$-$Y_p$—$Z_q$-AM-MBHA-®, wherein $AA_1$ is -L-Tyr-, -L-Thr- or -L-Ser-; $AA_2$ is -L-Pro- or -L-Val-; $AA_3$ is -L-Ala- or -L-Gly-; $AA_4$ is -L-Val-, -L-Glu- or -Gly-; $AA_5$ is -L-Ala- or -Gly-; $AA_6$ is -L-Pro-, -L-His-, -Gly- or -L-Gln-; and n, m, p and q are 0.

6.85 g of the Fmoc-AM-MBHA resin with a functionalization of 0.73 mmol/g (5 mmol) is treated with piperidine-DMF according to the described general protocol in order to remove the Fmoc group. 4.22 g of Fmoc-L-Pro-OH, 7.75 g of Fmoc-L-His(Trt)-OH, 3.72 g of Fmoc-Gly-OH or 7.63 g of Fmoc-L-Gln(Trt)-OH (12.5 mmol; 2.5 equiv) are incorporated onto the deprotected resin in the presence of DIPCDI (1.93 mL; 12.5 mmol; 2.5 equiv) and HOBt (1.93 g; 12.5 mmol; 2.5 equiv) using DMF as a solvent for 1 hour.

The resins are then washed as described in the general methods and the deprotection treatment of the Fmoc group is repeated to couple the next amino acid. Following the previously described protocols 3.72 g of Fmoc-Gly-OH or 4.12 g of Fmoc-L-Ala-OH (12.5 mmol; 2.5 equiv); 4.24 g of Fmoc-L-Val-OH, 5.54 g of Fmoc-L-Glu(OtBu)-OH or 3.72 g of Fmoc-Gly-OH (12.5 mmol; 2.5 equiv); 3.72 g of Fmoc-Gly-OH or 4.12 g of Fmoc-L-Ala-OH (12.5 mmol; 2.5 equiv); 4.24 g of Fmoc-L-Val-OH or 4.22 g of Fmoc-L-Pro-OH (12.5 mmol; 2.5 equiv); and subsequently 5.74 g of Fmoc-L-Tyr(tBu)-OH, 4.97 g of Fmoc-L-Thr(tBu)-OH or 4.79 g of Fmoc-L-Ser(tBu)-OH (12.5 mmol; 2.5 equiv) is coupled sequentially, each coupling in the presence of 1.93 g of HOBt (12.5 mmol; 2.5 equiv) and 1.93 mL of DIPCDI (12.5 mmol; 2.5 equiv).

After the synthesis, the peptidyl resins are washed with DCM (5×3 min) and dried by nitrogen stream.

Example 3 (Prophetic)

General Process for Removal of Fmoc N-Terminal Protective Group

The N-terminal Fmoc group of the peptidyl resins obtained in examples 1 and 2 is deprotected as described in the general methods (20% piperidine in DMF, 1×5 min+1×20 min). The peptidyl resins are washed with DMF (5×1 min), DCM (4×1 min), diethyl ether (4×1 min) and dried under vacuum.

Example 4 (Prophetic)

Process for Introducing the $R_1$ Palmitoyl Group onto the Peptidyl Resins Obtained in Example 3

2.56 g of palmitic acid (10 mmol; 10 equiv) pre-dissolved in DMF (1 mL) is added onto 1 mmol of the peptidyl resins obtained in Example 3, in the presence of 1.53 g of HOBt (10 mmol; 10 equiv) and 1.54 mL of DIPCDI (10 mmol; 10 equiv). They are allowed to react for 15 hours, after which the resins are washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and are dried under vacuum.

Example 5 (Prophetic)

Process for Introducing the $R_1$ Acetyl Group onto the Peptidyl Resins Obtained in Example 3

1 mmol of the peptidyl resins obtained in Example 3 is treated with 25 equiv of acetic anhydride in the presence of 25 equiv of DIEA using 5 mL of DMF as a solvent. They are allowed to react for 30 mins, after which the peptidyl resins were washed with DMF (5×1 min), DCM (4×1 min), diethyl ether (4×1 min) and are dried under vacuum.

Example 6 (Prophetic)

Cleavage Process from the Polymeric Support of the Peptidyl Resins Obtained in Examples 3, 4 and 5

200 mg of the dried peptidyl resins obtained in Examples 3, 4 and 5 is treated with 5 mL of TFA:TIS:$H_2O$ (90:5:5) for 2 hours at room temperature under stirring. The filtrates are collected onto 50 mL cold diethyl ether, they were filtered through polypropylene syringes fitted with porous polyethylene discs and washed 5 times with 50 mL diethyl ether. The final precipitates are dried under vacuum.

HPLC analysis of the obtained peptides in gradients of MeCN (+0.07% TFA) in $H_2O$ (+0.1% TFA) shows a purity exceeding 80% in all cases. The identity of the peptides obtained is confirmed by ESI-MS.

Example 7 (Prophetic)

Cleavage Process of the Polymeric Support and Functionalization with $R_2$ Substituted Amine: Obtaining Fmoc-$W_n$—$X_m$-$AA_1$-$AA_2$-$AA_3$-$AA_4$-$AA_5$-$AA_6$-$Y_p$—$Z_q$—NH—$(CH_2)_{15}$—$CH_3$, Wherein $AA_1$ is -L-Tyr-, -L-Thr- or -L-Ser-; $AA_2$ is -L-Pro- or -L-Val-; $AA_3$ is -Gly- or -L Ala-; $AA_4$ is -L-Val-, -L-Glu- or -Gly-; $AA_5$ is -Gly- or -L-Ala-; $AA_6$ is -L-Pro-, -L-His-, -Gly- or -L-Gln-; and n, m, p and q are 0

The peptides Ac—$W_n$—$X_m$-$AA_1$-$AA_2$-$AA_3$-$AA_4$-$AA_5$-$AA_6$-$Y_p$—$Z_q$—OH with fully protected side chains are obtained by treating 150 mg of the peptidyl resins Ac—$W_n$—$X_m$-$AA_1$-$AA_2$-$AA_3$-$AA_4$-$AA_5$-$AA_6$-$Y_p$—$Z_q$—O-2-ClTrt-® of Example 5, previously desiccated under vacuum in the presence of KOH, with 3 mL of a 3% solution of TFA in DCM for 5 min. The filtrates are collected onto 50 mL of cold diethyl ether and the treatment is repeated three times. Ethereal solutions are evaporated to dryness at reduced pressure and room temperature, the precipitates are redissolved in 50% MeCN in $H_2O$ and lyophilized. 10 mg of the obtained crude peptides are weighed in a flask and 3 equiv of hexadecylamine and 25 mL of anhydrous DMF is added. 2 equiv of DIPCDI is added, and left to react being magnetically stirred at 47° C. The reactions are monitored by HPLC until disappearance of the initial products, which are complete after 24-48 hours. Solvents are evaporated to dryness and co-evaporated twice with DCM. The obtained residues [Ac—$W_n$—$X_m$-$AA_1$-$AA_2$-$AA_3$-$AA_4$-$AA_5$-$AA_6$-$Y_p$—$Z_q$—NH—$(CH_2)_{15}$—$CH_3$ with fully protected side chains] are redissolved in 25 mL of a mixture of TFA-DCM-anisole (49:49:2) and left to react for 30 min at room temperature. 250 mL of cold diethyl ether are added, the solvents are evaporated under reduced pressure and two additional co-evaporations with ether are carried out. The residues are dissolved in a mixture of 50% MeCN in $H_2O$ and lyophilized.

HPLC analysis of the obtained peptides in gradients of MeCN (+0.07% TFA) in $H_2O$ (+0.1% TFA) shows a purity exceeding 60% in all cases. The identity of the peptides obtained is confirmed by ESI-MS.

Example 8

Modulation of the Human AQP-3 Promoter Activity

The modulation capacity of the promoter of the AQP-3 gene was evaluated in a cell line of keratinocytes stably transfected with the luciferase gene under the regulation of the human AQP-3 promoter. 20,000 to 30,000 cells per well were seeded and incubated for 24 hours in DMEM medium, after which the peptides of the invention were added at 0.5 mg/mL and were incubated for another 16-24 hours. The DMEM medium (carrier) was used as a negative control. The measurement of the promoter's activity was carried out using the Steady-Glo® Luciferase Assay System (PROMEGA) kit following the manufacturer's instructions. The luminescence values were read on a luminometer at 630 nm and the activity of the promoter was determined, which was normalized with regards to the values of the negative control.

Table 2 details the peptides which showed values of stimulation of the activity of the human AQP-3 promoter above 10% in the conditions tested.

TABLE 2

Modulation of the activity of human AQP-3 promoter

| Treatment | Activity of the AQP-3 promoter (%) |
|---|---|
| Carrier | 100% |
| Ac-L-Ser-L-Val-L-Ala-Gly-Gly-Gly-$NH_2$ (Ac-SEQ ID 38-$NH_2$) | 156% |
| Ac-L-Ser-L-Pro-L-Ala-Gly-Gly-L-Gln-$NH_2$ (Ac-SEQ ID 8-$NH_2$) | 152% |
| Ac-L-Tyr-L-Val-L-Ala-Gly-Gly-L-Pro-$NH_2$ (Ac-SEQ ID 35-$NH_2$) | 150% |
| Ac-L-Ser-L-Val-L-Ala-Gly-Gly-L-Pro-$NH_2$ (Ac-SEQ ID 13-$NH_2$) | 144% |
| Ac-L-Ser-L-Val-L-Ala-L-Glu-Gly-L-Gln-$NH_2$ (Ac-SEQ ID 12-$NH_2$) | 138% |
| Ac-L-Tyr-L-Val-L-Ala-Gly-Gly-L-His-$NH_2$ (Ac-SEQ ID 34-$NH_2$) | 136% |
| Ac-L-Tyr-L-Pro-L-Ala-L-Glu-Gly-L-Gln-$NH_2$ (Ac-SEQ ID 22-$NH_2$) | 135% |
| Ac-L-Tyr-L-Val-L-Ala-L-Glu-Gly-L-Pro-$NH_2$ (Ac-SEQ ID 32-$NH_2$) | 135% |
| Ac-L-Ser-L-Pro-L-Ala-Gly-Gly-L-Pro-$NH_2$ (Ac-SEQ ID 10-$NH_2$) | 135% |
| Ac-L-Ser-L-Pro-L-Ala-L-Val-Gly-L-Gln-$NH_2$ (Ac-SEQ ID 39-$NH_2$) | 133% |
| Ac-L-Tyr-L-Pro-L-Ala-Gly-Gly-Gly-$NH_2$ (Ac-SEQ ID 25-$NH_2$) | 132% |
| Ac-L-Tyr-L-Pro-L-Ala-L-Val-Gly-L-Gln-$NH_2$ (Ac-SEQ ID 28-$NH_2$) | 129% |
| Ac-L-Ser-L-Val-L-Ala-L-Val-Gly-L-Gln-$NH_2$ (Ac-SEQ ID 15-$NH_2$) | 129% |
| Ac-L-Tyr-L-Val-L-Ala-Gly-Gly-Gly-$NH_2$ (Ac-SEQ ID 33-$NH_2$) | 129% |
| Ac-L-Ser-L-Val-L-Ala-L-Val-Gly-Gly-$NH_2$ (Ac-SEQ ID 16-$NH_2$) | 127% |
| Ac-L-Ser-L-Pro-L-Ala-L-Val-Gly-Gly-$NH_2$ (Ac-SEQ ID 40-$NH_2$) | 126% |
| Ac-L-Tyr-L-Pro-L-Ala-L-Glu-Gly-Gly-$NH_2$ (Ac-SEQ ID 23-$NH_2$) | 125% |
| Ac-L-Tyr-L-Pro-L-Ala-L-Val-Gly-Gly-$NH_2$ (Ac-SEQ ID 29-$NH_2$) | 125% |
| Ac-L-Ser-L-Pro-L-Ala-L-Glu-Gly-Gly-$NH_2$ (Ac-SEQ ID 6-$NH_2$) | 124% |
| Ac-L-Ser-L-Val-L-Ala-Gly-Gly-L-His-$NH_2$ (Ac-SEQ ID 41-$NH_2$) | 124% |
| Ac-L-Tyr-L-Val-L-Ala-Gly-Gly-L-Gln-$NH_2$ (Ac-SEQ ID 42-$NH_2$) | 123% |

TABLE 2-continued

Modulation of the activity of human AQP-3 promoter

| Treatment | Activity of the AQP-3 promoter (%) |
|---|---|
| Ac-L-Tyr-L-Pro-L-Ala-Gly-Gly-L-Gln-NH$_2$(Ac-SEQ ID 43-NH$_2$) | 122% |
| Ac-L-Tyr-L-Pro-L-Ala-L-Val-Gly-L-Pro-NH$_2$(Ac-SEQ ID 31-NH$_2$) | 122% |
| Ac-L-Ser-L-Pro-L-Ala-L-Glu-Gly-L-Gln-NH$_2$(Ac-SEQ ID 5-NH$_2$) | 121% |
| Ac-L-Tyr-L-Pro-L-Ala-L-Val-Gly-L-His-NH$_2$(Ac-SEQ ID 30-NH$_2$) | 121% |
| Ac-L-Tyr-L-Pro-L-Ala-L-Glu-Gly-L-Pro-NH$_2$(Ac-SEQ ID 24-NH$_2$) | 121% |
| Ac-L-Ser-L-Val-L-Ala-L-Val-Gly-L-Pro-NH$_2$(Ac-SEQ ID 17-NH$_2$) | 121% |
| Ac-L-Tyr-L-Val-L-Ala-L-Val-Gly-Gly-NH$_2$(Ac-SEQ ID 36-NH$_2$) | 120% |
| Ac-L-Tyr-L-Val-L-Ala-L-Glu-Gly-L-His-NH$_2$(Ac-SEQ ID 44-NH$_2$) | 120% |
| Ac-L-Ser-L-Pro-L-Ala-Gly-Gly-L-His-NH$_2$(Ac-SEQ ID 45-NH$_2$) | 120% |
| Ac-L-Ser-L-Val-L-Ala-L-Glu-Gly-Gly-NH$_2$(Ac-SEQ ID 46-NH$_2$) | 119% |
| Ac-L-Ser-L-Pro-L-Ala-L-Glu-Gly-L-His-NH$_2$(Ac-SEQ ID 48-NH$_2$) | 117% |
| Ac-L-Ser-L-Pro-L-Ala-L-Val-Gly-L-Pro-NH$_2$(Ac-SEQ ID 49-NH$_2$) | 116% |
| Ac-L-Ser-L-Val-L-Ala-Gly-Gly-L-Gln-NH$_2$(Ac-SEQ ID 50-NH$_2$) | 115% |
| Ac-L-Tyr-L-Pro-L-Ala-Gly-Gly-L-Pro-NH$_2$(Ac-SEQ ID 26-NH$_2$) | 114% |
| Ac-L-Tyr-L-Val-L-Ala-L-Glu-Gly-Gly-NH$_2$(Ac-SEQ ID 56-NH$_2$) | 112% |
| Ac-L-Ser-L-Val-L-Ala-L-Glu-Gly-L-His-NH$_2$(Ac-SEQ ID 58-NH$_2$) | 112% |

Example 9

Effect of the Peptides Ac-L-Tyr-L-Pro-L-Ala-L-Glu-Gly-L-Gln-NH$_2$ (Ac-SEQ ID 22-NH$_2$), Ac-L-Ser-L-Val-L-Ala-L-Val-Gly-L-Gln-NH$_2$ (Ac-SEQ ID 15-NH$_2$), and Ac-L-Ser-L-Pro-L-Ala-Gly-Gly-L-Pro-NH$_2$(Ac-SEQ ID 10-NH$_2$) on the Transcription of the AQP-3 Gene The expression levels of the gene AQP-3 were measured by PCR in quantitative real time. A human keratinocyte cell line from adult skin was incubated at a density of 10,000 to 20,000 cells per well in EpiLife™ medium (Cascade Biologics) for 3-5 days and they were subsequently incubated with the peptides of the invention for another 16-24 hours, after which the cells were lysed and the RNA was extracted. The PCR was carried out in quantitative real time using the Taqman® Gene Expression Cells-to-CT (Applied Biosystems) kit according to the manufacturer's instructions and with the appropriate probes (TaqMan® Hs00185020_m1 probe for the AQP-3 gene and Taqman® Hs99999901_s1 probe for the eukaryotic ribosomal subunit 18S, the endogenous control of expression) and the values were normalized with regards to the basal levels of AQP-3 mRNA of the untreated cells (carrier).

Table 3 shows the relative quantification values of mRNA of the AQP-3 gene after incubation with the different peptides at the stated concentrations.

TABLE 3

Relative quantification of AQP-3 mRNA in human epidermal keratinocytes

| Treatment | % relative quantity AQP-3 mRNA |
|---|---|
| Carrier | 100% |
| 0.1 mg/mL Ac-L-Tyr-L-Pro-L-Ala-L-Glu-Gly-L-Gln-NH$_2$(Ac-SEQ ID 22-NH$_2$) | 229% |
| 0.1 mg/mL Ac-L-Ser-L-Val-L-Ala-L-Val-Gly-L-Gln-NH$_2$(Ac-SEQ ID 15-NH$_2$) | 162% |
| 0.1 mg/mL Ac-L-Ser-L-Pro-L-Ala-Gly-Gly-L-Pro-NH$_2$(Ac-SEQ ID 10-NH$_2$) | 200% |

Example 10

Stimulation of Collagen Type I Synthesis in Human Dermal Fibroblasts

The ability of the peptides of the invention to stimulate collagen type I synthesis in human dermal fibroblasts (HDFa, Cascade Biologics) was evaluated in culture using ELISA (enzyme-linked immunosorbent assay). The fibroblasts grew in M106 supplemented with specific factors for their growth. 50,000 cells per well were seeded and incubated at 37° C., 5% $CO_2$, with humidified air. After 24 hours the peptides of the invention were added, and were incubated for another 48 hours, after which the supernatants were collected.

96-well plates were covered with 50 μL of a standard bovine collagen type I (Sigma) or with the previously collected supernatants. The collagen was absorbed onto the wells throughout the night at 4° C. in a humidified atmosphere. The plates were washed three times and were blocked for one hour with 3% bovine serum albumin, after which they were incubated with a primary anti-collagen type I anti-body (Sigma) for 2 hours. Subsequently, the secondary antibody, goat anti-mouse IgG-HRP (Molecular Probes) was added. The plates were incubated with the phosphate substrate for 30 minutes under stirring and the reaction was stopped by adding 3 M of $H_2SO_4$. The absorbance was measured at 490 nm in a plate reader (Genios, Tecan) and the concentration of collagen was determined by comparing it with a standard linear regression line.

TABLE 4

Stimulation of collagen type I synthesis

| Treatment | % Increase in collagen type I synthesis |
| --- | --- |
| Carrier | 0% |
| 0.01 mg/ mL Ac-L-Ser-L-Pro-L-Ala-Gly-Gly-L-Pro-NH$_2$(Ac-SEQ ID 10-NH$_2$) | 36% |
| 0.1 mg/ mL Ac-L-Ser-L-Pro-L-Ala-Gly-Gly-L-Pro-NH$_2$(Ac-SEQ ID 10-NH$_2$) | 58% |

Example 11

Effect of Ac-L-Ser-L-Pro-L-Ala-Gly-Gly-L-Pro-NH$_2$ (Ac-SEQ ID 10-NH$_2$) on the Proliferation of Human Epidermal Keratinocytes Cell proliferation was evaluated by a fluorescence-based cell viability method, in which the live cells are distinguished from the dead cells by the enzymatic conversion of calcein-AM to its fluorescent form.

Human keratinocytes were cultivated in DMEM supplemented with fetal bovine serum (FBS, Cultek) until confluence is achieved. The cells were then separated using trypsin and were seeded in 96-well plates. After 24 hours of incubation in DMEM at 37° C. in a humidified atmosphere at 5% $CO_2$ a fresh medium was added with different concentrations of the product of the invention. Cells treated with DMEM as a negative control were used. The cells were incubated for another 24 hours under the same conditions and the medium was substituted by 100 μl of calcein-AM (Molecular Probes) at 0.4 μM diluted in phosphate buffered saline (PBS, Sigma). After 30 minutes of incubation at 37° C. the fluorescence was measured at excitation 485 nm 1 and emission 530 nm ($\lambda_{em}$) in a plate reader (Genios Tecan). The total growth percentage was calculated as T/C×100 wherein T is the fluorescence of the wells treated with the peptides of the invention and C the fluorescence of the control wells treated with DMEM.

Table 5 shows the values of the stimulation of epidermal keratinocyte proliferation after incubation with the peptides of the invention at the stated concentrations.

TABLE 5

Proliferation of human epidermal keratinocytes

| Treatment | % Stimulation of proliferation |
| --- | --- |
| Carrier | 0% |
| 0.16 mg/ mL Ac-L-Ser-L-Pro-L-Ala-Gly-Gly-L-Pro-NH$_2$(Ac-SEQ ID 10-NH$_2$) | 24% |
| 0.62 mg/ mL Ac-L-Ser-L-Pro-L-Ala-Gly-Gly-L-Pro-NH$_2$(Ac-SEQ ID 10-NH$_2$) | 28% |
| 2.50 mg/ mL Ac-L-Ser-L-Pro-L-Ala-Gly-Gly-L-Pro-NH$_2$(Ac-SEQ ID 10-NH$_2$) | 31% |

The peptide Ac-L-Ser-L-Pro-L-Ala-Gly-Gly-L-Pro-NH$_2$ (Ac-SEQ ID 10-NH$_2$) stimulated the proliferation of human keratinocytes by 31% at 2.5 mg/mL, therefore improving the skin barrier function.

Example 12 (Prophetic)

Preparation of Coacervates of Nanostructured Lipid Carriers Containing Ac-L-Tyr-L-Pro-L-Ala-L-Glu-Gly-L-Gln-NH$_2$(Ac-SEQ ID 22-NH$_2$)

In a suitable vessel the following are added in this order: water [INCI: Water (Aqua)], hydroxypropyl starch phosphate [INCI: Hydroxypropyl Starch Phosphate], sclerotium gum [INCI: Sclerotium Gum], sodium hyaluronate [INCI: Sodium Hyaluronate], propanediol [INCI: Propanediol], phenoxyethanol [INCI: Phenoxyethanol] (phase A ingredients). The mixture of ingredients from phase A is heated to 65° C.

In another vessel sorbitan sesquiolate [INCI: Sorbitan Sesquiolate], and isohexadecane [INCI: Isohexadecane] are added (phase B ingredients) and are dissolved at 60-65° C.

In a third vessel water [INCI: Water (Aqua)], Ac-L-Tyr-L-Pro-L-Ala-L-Glu-Gly-L-Gln-NH$_2$ (Ac-SEQ ID 22-NH$_2$), soybean oil [INCI: Soybean (Glycine Soja) Oil], sorbitan tristearate [INCI: Sorbitan Tristearate] and cetyl PEG/PPG-10/1 dimethicone [INCI: Cetyl PEG/PPG-10/1 Dimethicone] are mixed (phase B1 ingredients).

In another vessel water [INCI: Water (Aqua)] and Quat-soy LDMA-25 [INCI: Water (Aqua), Lauryldimonium Hydroxypropyl Hydrolyzed Soy Protein] are mixed (phase C ingredients).

In another vessel hydroxypropyl starch phosphate [INCI: Hydroxypropyl Starch Phosphate], sclerotium gum [INCI: Sclerotium Gum] are mixed (phase D ingredients).

Phase B1 is added to phase B. The mixture is added to phase A under constant stirring and is microfluidified. Phase C and phase D are added under constant stirring, obtaining a composition with the proportions shown in Table 6.

TABLE 6

Coacervates of nanostructured lipid carriers

| Phase | INGREDIENT | % in weight |
|---|---|---|
| A | WATER (AQUA) | q.s.p. 100 |
| A | HYDROXYPROPYL STARCH PHOSPHATE | 1 |
| A | SCLEROTIUM GUM | 0.5 |
| A | SODIUM HYALURONATE | 0.01 |
| A | PROPANEDIOL | 5 |
| A | PHENOXYETHANOL | 2.6 |
| B | SORBITAN SESQUIOLEATE | 4 |
| B | ISOHEXADECANE | 5 |
| B1 | WATER (AQUA) | 16.75 |
| B1 | Ac-L-Tyr-L-Pro-L-Ala-L-Glu-Gly-L-Gln-NH$_2$(Ac-SEQ ID 22-NH$_2$) | 0.05 |
| B1 | SOYBEAN (GLYCINE SOJA) OIL | 11.1 |
| B1 | SORBITAN TRISTEARATE | 0.6 |
| B1 | CETYL PEG/PPG-10/1 DIMETHICONE | 1.5 |

TABLE 6-continued

Coacervates of nanostructured lipid carriers

| Phase | INGREDIENT | % in weight |
|---|---|---|
| C | WATER (AQUA) | 6 |
| C | QUAT-SOY LDMA-25 | 0.2 |
| D | HYDROXYPROPYL STARCH PHOSPHATE | 1.5 |
| D | SCLEROTIUM GUM | 0.75 |

Example 13

Preparation of a Water in Oil Microemulsion (w/o) Containing Ac-L-Ser-L-Val-L-Ala-L-Val-Gly-L-Gln-NH$_2$(Ac-SEQ ID 15-NH$_2$)

In a suitable vessel caprylic/capric triglyceride [INCI: Caprylic/Capric Triglyceride], oleic acid [INCI: Oleic Acid], Edenor LS2M GS [INCI: Stearic Acid, Palmitic Acid] and ceramide [INCI: Ceramide 3] were added (phase A1 ingredients), and the mixture was heated to 80-85° C.

Beta sitosterol [INCI: Beta-Sitosterol] (phase A2) and Glycosylceramides IRB3 [INCI: Lecithin, Glycolipids] (phase A3) were added under constant stirring and the mixture was left to cool to 40° C.

Evening primrose oil [INCI: Evening Primrose (Oenothera biennis) Oil], borage seed oil [INCI: Borago Officinalis Seed Oil], Vitamin F Glyceryl Ester CLR™ [INCI: Glyceryl Linoleate, Glyceryl Linolenate], and tocopheryl acetate [INCI: Tocopheryl Acetate] were mixed under stirring (phase B ingredients) and it was mixed with phase A at 40° C.

In a separate vessel isostearic acid [INCI: Isostearic Acid] and Empipearl XA 500™ [INCI: Water (Aqua), Sodium Laureth Sulfate, Glycol Cetearate, Cocamide DEA, Formaldehyde] were mixed under stirring (phase C ingredients) and then denatured alcohol was added [INCI: Alcohol Denat], Ac-L-Ser-L-Val-L-Ala-L-Val-Gly-L-Gln-NH$_2$ (Ac-SEQ ID 15-NH$_2$) (phase C1 ingredients). This mixture of phases C and C1 was added into the first mixture of phase A1, A2, A3 and phase B under constant stirring, obtaining a cosmetic composition with the proportions shown in Table 7.

TABLE 7

Microemulsion

| Phase | INGREDIENT | % weight |
|---|---|---|
| A1 | CAPRYLIC/CAPRIC TRIGLYCERIDE | q.s.p. 100 |
| A1 | OLEIC ACID | 0.018 |
| A1 | EDENOR L2SM GS | 0.0045 |
| A1 | CERAMIDE 3 | 0.0045 |
| A2 | BETA SITOSTEROL | 0.0225 |
| A3 | GLYCOSYLCERAMIDES IRB 3 | 0.0135 |
| B | EVENING PRIMROSE (OENOTHERA BIENNIS) OIL | 9 |
| B | BORAGO OFFICINALIS SEED OIL | 9 |
| B | VITAMIN F GLYCERYL ESTER CLR | 4.5 |
| B | TOCOPHERYL ACETATE | 0.45 |

TABLE 7-continued

Microemulsion

| Phase | INGREDIENT | % weight |
|---|---|---|
| C | ISOSTEARIC ACID | 7.86 |
| C | EMPIPEARL XA 500 | 1.39 |
| C1 | ALCOHOL DENAT. | 0.746 |
| C1 | Ac-L-Ser-L-Val-L-Ala-L-Val-Gly-L-Gln-NH$_2$ (Ac-SEQ ID 15-NH$_2$) | 0.001 |

Example 14

Preparation of a Cosmetic Facial Composition Containing Ac-L-Ser-L-Pro-L-Ala-Gly-Gly-L-Pro-NH$_2$ (Ac-SEQ ID 10-NH$_2$)

In a suitable vessel water [INCI: Water (Aqua)], Pentylene glycol [INCI: Pentylene Glycol], and benzyl alcohol [INCI: Benzyl Alcohol] were mixed together (phase A ingredients). Carbomer [INCI: Carbomer] (phase A1 ingredient) and potassium cetyl phosphate [INCI: Potassium Cetyl Phosphate] were added (phase A2 ingredient) to phase A under constant stirring until it was completely dissolved. The mixture was heated to 65-70° C.

Ethylhexyl cocoate [INCI: Ethylhexyl Cocoate], C12-C15 alkyl benzoate [INCI: C12-15 Alkyl Benzoate], Phytocream 2000™ [INCI: Glyceryl Stearate, Cetearyl Alcohol, Potassium Palmitoyl Hydrolyzed Wheat Protein] Phenoxyethanol [INCI: Phenoxyethanol], Tocopheryl acetate [INCI: Tocopheryl Acetate] and Dimethicone [INCI: Dimethicone] were weighed in another vessel (phase B ingredients) and the mixture was mixed together at 65-70° C. Phase B was added to phase A. It was cooled and Sepigel 305™ [INCI: Polyacrylamide, Water (Aqua), C13-14 Isoparaffin, Laureth-7] was added to it (phase C ingredients) under constant stirring. The pH was adjusted with sodium hydroxide [INCI: Sodium Hydroxide (20% in aqueous solution)] (phase D ingredient) and fragrance was added (phase E). Ac-L-Ser-L-Pro-L-Ala-Gly-Gly-L-Pro-NH$_2$ (Ac-SEQ ID 10-NH$_2$) was added (phase F) under stirring, obtaining a cosmetic composition with the proportions shown in Table 8.

TABLE 8

Facial cosmetic composition

| Phase | INGREDIENT | % weight |
|---|---|---|
| A | WATER (AQUA) | q.s.p. 100 |
| A | PENTYLENE GLYCOL | 4.9 |
| A | BENZYL ALCOHOL | 0.98 |
| A1 | CARBOMER | 0.49 |
| A2 | POTASSIUM CETYL PHOSPHATE | 0.49 |
| B | ETHYLHEXYL COCOATE | 2.45 |
| B | C12-15 ALKYL BENZOATE | 4.9 |
| B | PHYTOCREAM 2000 | 4.9 |
| B | PHENOXYETHANOL | 0.88 |
| B | TOCOPHERYL ACETATE | 0.49 |
| B | DIMETHICONE | 0.98 |
| C | SEPIGEL 305 | 0.98 |
| D | SODIUM HYDROXIDE (20% in aqueous solution) | c.s. |
| E | FRAGRANCE (PARFUM) | 0.098 |
| F | Ac-L-Ser-L-Pro-L-Ala-Gly-Gly-L-Pro-NH$_2$ (Ac-SEQ ID 10-NH$_2$) | 0.001 |

Example 15

Effect of the Composition of Example 14 on the Treatment of Dry Skin

A study of cutaneous hydration was carried out on 20 Caucasian women between 30 and 50 years of age, with an average age of 43.1 years, with dry skin. For the whole duration of the study the subjects did not use any other different product on the tested areas and avoided exposure to UV radiation. The volunteers applied the composition from Example 14 to one half of their face and a placebo composition (the same composition from Example 14 without the peptide) to the other half, twice a day for 56 days. Cutaneous hydration was instrumentally assessed before and after the treatment using a Courage & Khazaka corneometer CM 825. The values obtained from the measurements are directly proportional to the quantity of water contained in the stratum corneum and represent the level of hydration of the cutaneous surface.

The study was carried out in a bioclimatic room (24±2° C.; 50±10% atmospheric humidity) with the aim of maintaining the temperature and humidity constant during the measuring. The average values and the standard deviations for the instrumental values of hydration were calculated for each measurement. For each measurement point the increase in cutaneous hydration was determined with regards to cutaneous hydration at the beginning of the study and the increase in cutaneous hydration provided by the formulation from Example 14 was calculated with regards to the increase in hydration provided by the placebo formulation.

The statistical analysis of the change in the parameters measured during the study was carried out using the Bonferroni test. The statistical significance threshold was established at 5%.

The increase in cutaneous hydration obtained by treating the skin with the cream from Example 14 is shown in Table 9.

TABLE 9

| | Change to hydration Placebo cream | Change to hydration Cream from Example 14 | Increase in the change to hydration |
|---|---|---|---|
| $T_{2h}-T_{0h}$ | 9.3 c.u. | 12.8 c.u. | +37.6% |
| $T_{8h}-T_{0h}$ | 6.6 c.u. | 13.7 c.u. | +107.6% |
| $T_{56days}-T_{0h}$ | 4.2 c.u. | 9.7 c.u. | +130.9% |

The results obtained show that the formulation from Example 14 hydrates the skin by 37.6% more than the placebo formulation after 2 hours, 107.6% more after 8 hours and 130.9% more after 56 days.

The invention claimed is:

1. A peptide of general formula (I)

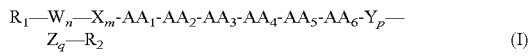

$$R_1-W_n-X_m-AA_1-AA_2-AA_3-AA_4-AA_5-AA_6-Y_p-Z_q-R_2 \quad (I)$$

its stereoisomers, mixtures thereof and/or its cosmetic or pharmaceutical acceptable salts, wherein:

$AA_1$ is selected from the group consisting of -Ser-, -Thr- and -Tyr-;
$AA_2$ is selected from the group consisting of -Pro- and -Val-;
$AA_3$ is -Ala-;
$AA_4$ is selected from the group consisting of -Glu-, -Gly- and -Val-;
$AA_5$ is -Gly-;
$AA_6$ is selected from the group consisting of -Gln-, -Gly-, -His- and -Pro-;
W, X, Y, Z are amino acids and are independently selected from amongst themselves;
n, m, p and q are independently selected from amongst themselves and have a value of 0 or 1;
n+m+p+q is lower than or equal to 2;
$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl, and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
with the condition that $R_1$ and $R_2$ are not α-amino acids.

2. The peptide according to claim 1, wherein $R_1$ is selected from the group consisting of H and $R_5$—CO—, wherein $R_5$ is selected from the group consisting of substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocycyl with 3-10 ring members, and substituted or unsubstituted heteroarylalkyl of 2 to 24 carbon atoms and 1 to 3 atoms other than carbon and an alkyl chain of 1 to 6 carbon atoms.

3. The peptide according to claim 2, wherein $R_1$ is selected from the group consisting of H, acetyl, tert-butanol, hexanoyl, 2-methylhexanoyl, cyclohexanecarboxyl, octanoyl, decanoyl, lauroyl, myristoyl, palmitoyl, stearoyl, oleoyl and linoleoyl.

4. The peptide according to claim 1, wherein $R_2$ is —$NR_3R_4$ or —$OR_3$, wherein $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocycyl with 3-10 ring members, and substituted or unsubstituted heteroarylalkyl of 2 to 24 carbon atoms and 1 to 3 atoms other than carbon and an alkyl chain of 1 to 6 carbon atoms.

5. The peptide according to claim 4, wherein $R_3$ and $R_4$ are independently selected from the group consisting of H, methyl, ethyl, hexyl, dodecyl, and hexadecyl.

6. The peptide according to claim 1, characterized in that $R_1$ is selected from the group consisting of H, acetyl, lauroyl, myristoyl, and palmitoyl, $AA_1$ is -L-Tyr-, $AA_2$ is -L-Pro-, $AA_3$ is -L-Ala-, $AA_4$ is -L-Glu-, $AA_5$ is -L-Gly-, $AA_6$ is -L-Gln-, and $R_2$ is —$NR_3R_4$ or —$OR_3$, wherein $R_3$ and $R_4$ are independently selected from H, methyl, ethyl, hexyl, dodecyl, and hexadecyl.

7. The peptide according to claim 1, wherein $R_1$ is selected from the group consisting of H, acetyl, lauroyl, myristoyl, and palmitoyl, $AA_1$ is -L-Ser-, $AA_2$ is -L-Val-, $AA_3$ is -L-Ala-, $AA_4$ is -L-Val-, $AA_5$ is -L-Gly-, $AA_6$ is -L-Gln-, and $R_2$ is —$NR_3R_4$ or —$OR_3$, wherein $R_3$ and $R_4$ are independently selected from H, methyl, ethyl, hexyl, dodecyl, and hexadecyl.

8. The peptide according to claim 1, wherein $R_1$ is selected from the group consisting of H, acetyl, lauroyl, myristoyl, and palmitoyl, $AA_1$ is -L-Ser-, $AA_2$ is -L-Pro-, $AA_3$ is -L-Ala-, $AA_4$ is -L-Gly-, $AA_5$ is -L-Gly-, $AA_6$ is -L-Pro-, and $R_2$ is —$NR_3R_4$ or —$OR_3$, wherein $R_3$ and $R_4$ are independently selected from H, methyl, ethyl, hexyl, dodecyl, and hexadecyl.

9. A process for the preparation of a peptide of general formula (I), its stereoisomers, mixtures thereof and/or its cosmetically or pharmaceutically acceptable salts, according to claim 1, wherein the preparation process is carried out by solid phase synthesis or in solution.

10. A cosmetic or pharmaceutical composition which comprises a cosmetically or pharmaceutically effective amount of at least one peptide of general formula (I), its stereoisomers, mixtures thereof and/or its cosmetically or pharmaceutically acceptable salts, according to claim 1, and at least one cosmetically or pharmaceutically acceptable excipient or agent.

11. The composition according to claim 10, wherein the peptide of general formula (I), its stereoisomers, mixtures thereof and/or its cosmetically or pharmaceutically acceptable salts, is incorporated into a cosmetic or pharmaceutical delivery system or sustained release system selected from the group consisting of liposomes, mixed liposomes, oleosomes, niosomes, ethosomes, millicapsules, microcapsules, nanocapsules, nanostructured lipid carriers, sponges, cyclodextrins, vesicles, micelles, mixed micelles of surfactants, surfactant-phospholipid mixed micelles, millispheres, microspheres, nanospheres, liposheres, microemulsions, nanoemulsions, miniparticles, milliparticles, microparticles, nanoparticles and solid lipid nanoparticles, or is adsorbed on a cosmetically or pharmaceutically acceptable solid organic polymer or solid mineral support selected from the group consisting of talc, bentonite, silica, starch and maltodextrin.

12. The composition according to claim 10, wherein the peptide of general formula (I), its stereoisomers, mixtures thereof and/or its cosmetically or pharmaceutically acceptable salts is presented in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, soft capsules, hard capsules, tablets, sugar coated tablets, granules, chewing gum, solutions, suspensions, emulsions, syrups, elixirs, polysaccharide films, jellies and gelatins.

13. The composition according to claim 10, wherein the peptide of general formula (I), its stereoisomers, mixtures thereof and/or its cosmetically or pharmaceutically acceptable salts is incorporated into a product selected from the group consisting of under-eye concealers, make-up foundation, make-up removing lotions, make-up removing milks, eye shadows, lipsticks, lip gloss, lip protectors, and powders.

14. The composition according to claim 10, wherein the peptide of general formula (I), its stereoisomers, mixtures thereof and/or its cosmetically or pharmaceutically acceptable salts, is incorporated into a fabric, a non-woven fabric, or a medical device.

15. The composition according to claim 10, wherein the at least one agent is selected from the group consisting of other AQP-3 modulating agents, aquaporin modulating agents, proteins from the aquaporin family, other collagen synthesis stimulating agents, agents modulating PGC-1α synthesis, agents modulating the activity of PPARγ, agents which increase or reduce the triglyceride content of adipocytes, agents stimulating or delaying adipocyte differentiation, lipolytic agents or agents stimulating lipolysis, anti-cellulite agents, adipogenic agents, inhibitors of acetylcholine-receptor aggregation, agents inhibiting muscle contraction, anticholinergic agents, elastase inhibiting agents, matrix metalloproteinase inhibiting agents, melanin synthesis stimulating or inhibiting agents, whitening or depigmenting agents, propigmenting agents, self-tanning agents, antiaging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments or colorants, dyes, biopolymers, gelling polymers, thickening agents, surfactants, softening agents, binding agents, preservatives, anti-wrinkle agents, agents able to reduce or treat the bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, heat shock proteins, HSP70 synthesis stimulators, heat shock protein synthesis-stimulating agents, hyaluronic acid synthesis-stimulating agents, fibronectin synthesis-stimulating agents, sirtuin synthesis-stimulating agents, agents stimulating the synthesis of lipids and components of the stratum corneum, ceramides, fatty acids, agents that inhibit collagen degradation, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents that inhibit acetylcholinesterase, skin relaxant agents, glycosaminoglycan synthesis-stimulating agents, antihyperkeratosis agents, comedolytic agents, anti-psoriasis agents, anti-dermatitis agents, anti-eczema agents, DNA repair agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, antiperspirant agents, agents stimulating healing, coadjuvant healing agents, agents stimulating reepithelization, coadjuvant reepithelization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, perfumes, chelating agents, plant extracts, essential oils, marine extracts, agents obtained from a biofermentation process, mineral salts, cell extracts, sunscreens and organic or mineral photoprotective agents active against ultraviolet A and/or B rays, and mixtures thereof.

16. A method for the treatment of the skin and/or mucous membranes comprising administering to the skin or mucous membranes a cosmetically or pharmaceutically effective amount of at least one peptide of general formula (I), its stereoisomers, mixtures thereof and/or their cosmetically or pharmaceutically acceptable salts, according to claim 1.

17. A method for the modulation of AQP-3 comprising administration of a cosmetically or pharmaceutically effective amount of at least one peptide of general formula (I), its stereoisomers, mixtures thereof and/or their cosmetically or pharmaceutically acceptable salts, according to claim 1.

18. The method according to claim 16, wherein the administration provides a treatment of the skin and/or mucous membranes which stimulates collagen synthesis or hydrates the skin and/or mucous membranes or improves the skin barrier function or reepithelializes and/or heals the skin and/or mucous membranes.

19. The method according to claim 16, wherein the administration provides a treatment, delay, and/or repair of the signs of aging and/or photoaging of the skin.

20. The method according to claim 19, wherein the treatment, delay, and/or repair of the signs of aging and/or photoaging of the skin reduces and/or treats facial wrinkles.

21. The method according to claim 16, wherein the treatment of the skin and/or mucous membranes is a treatment of conditions, disorders and/or diseases of the skin and/or mucous membranes selected from the group consisting of psoriasis, dermatitis, atopic dermatitis, allergic dermatitis, eczema, spongiosis, edema, hereditary ichthyosis, senile xerosis, vaginal dryness, wrinkles, expression wrinkles, stretch marks, aged skin, photoaged skin, skin cancer, healing or reepithelization disorders, chronic ulcers, acne, hypertrophic scars, orange peel skin, keratosis, rosacea, telangiectasia, couperosis, bags under the eyes, periorbital dark circles, varicose veins, alopecia, gingivitis, periodontitis, and inflammatory processes.

* * * * *